US005775331A

United States Patent [19]

Raymond et al.

[11] Patent Number: 5,775,331
[45] Date of Patent: Jul. 7, 1998

[54] APPARATUS AND METHOD FOR LOCATING A NERVE

[75] Inventors: Stephen A. Raymond, Charlestown; David E. Coats, Newton, both of Mass.

[73] Assignees: UroMed Corporation, Needham; Brigham and Women's Hospital, Boston, both of Mass.

[21] Appl. No.: 484,390

[22] Filed: Jun. 7, 1995

[51] Int. Cl.[6] ........................................... A61B 5/05
[52] U.S. Cl. ........................................... 128/741
[58] Field of Search ........................... 128/741, 774, 128/782

[56] References Cited

U.S. PATENT DOCUMENTS

| | | | |
|---|---|---|---|
| 2,704,064 | 3/1955 | Fizzell et al. | 128/741 |
| 3,364,929 | 1/1968 | Ide et al. | 128/741 |
| 3,403,684 | 10/1968 | Stiebel et al. | 128/407 |
| 3,641,993 | 2/1972 | Gaarder et al. | 128/733 |
| 3,664,329 | 5/1972 | Naylor | 128/741 |
| 3,682,162 | 8/1972 | Coyler | 128/642 |
| 3,738,368 | 6/1973 | Avery et al. | 128/418 |
| 3,830,226 | 8/1974 | Staub et al. | 128/741 |
| 3,941,136 | 3/1976 | Bucalo | 128/422 |
| 4,099,519 | 7/1978 | Warren | 128/741 |
| 4,103,678 | 8/1978 | Karacan et al. | 128/774 |
| 4,124,028 | 11/1978 | Gallo | 128/407 |
| 4,207,897 | 6/1980 | Lloyd et al. | 606/23 |
| 4,291,705 | 9/1981 | Severinghaus et al. | 128/733 |
| 4,296,760 | 10/1981 | Carlsson et al. | 128/788 |
| 4,515,166 | 5/1985 | Timm | 128/694 |
| 4,515,168 | 5/1985 | Chester et al. | 128/741 |
| 4,542,753 | 9/1985 | Brenman et al. | 128/788 |
| 4,585,005 | 4/1986 | Lue et al. | 128/419 B |
| 4,663,102 | 5/1987 | Brenman et al. | 264/222 |
| 4,735,208 | 4/1988 | Wyler et al. | 128/642 |
| 4,777,952 | 10/1988 | Pavel | 128/419 S |
| 4,811,742 | 3/1989 | Hassell et al. | 128/733 |
| 4,815,475 | 3/1989 | Burger | 128/741 |
| 4,817,628 | 4/1989 | Zealear et al. | 128/741 |
| 4,848,361 | 7/1989 | Penney et al. | 128/774 |
| 4,892,105 | 1/1990 | Prass | 128/741 |
| 4,909,263 | 3/1990 | Norris | 128/788 |
| 4,913,162 | 4/1990 | Leang et al. | 128/774 |

(List continued on next page.)

OTHER PUBLICATIONS

Ford et al., "Electrical Characteristics . . . Localization," *Regional Anesth* 9:73–77 (1984).
Greenblatt et al, "Needle Nerve Stimulator–Locator," *Anest Analg* 41:599–602 (1962).
Pither et al., "The Use of Peripheral . . . Clinical Applications," *Regional Anesth* 10:49–58 (1985).
Raj. P., "The Use of Peripheral Nerve . . . Anesthesia," *Clinical Issues in Regional Anest* 1:1–6 (1985).
Raj et al., "Use of the Nerve Stimulator for Peripheral Blocks," *Regional Anest* 5:14–21 (1980).
Raj et al., "Infraclavicular Brachial Plexus Block—A New Approach," *Anesth Analg* 52:897–903 (1973).
Shafik, A., "Cavernous Nerve Stimulation . . . Penile Erection," *Eur Urol* 26:98–102 (1994).
Martin et al., Initiation of Erection . . . Probe ElectroStimulation (RPE), Martin and Associates (1983).

*Primary Examiner*—William E. Kamm
*Attorney, Agent, or Firm*—Sterne, Kessler, Goldstein & Fox P.L.L.C.

[57] ABSTRACT

An apparatus and method for stimulating and locating a nerve is described. The apparatus is closed-loop in nature in that the device is automated and is independent of the skill of the operator. The apparatus includes a stimulating probe having an array of electrodes, an automatic control means, and a response detecting means. Response feedback is analyzed according to an electrode selecting algorithm (incorporating a response interpreting algorithm) so that ongoing stimulation is restricted to a subset of the array which produces a criterion response with the least magnitude of stimulation. A method of use is also described. The device and method are also intended to permit optimal stimulation of a located nerve for therapeutic purposes.

99 Claims, 13 Drawing Sheets

U.S. PATENT DOCUMENTS

| | | | |
|---|---|---|---|
| 4,926,865 | 5/1990 | Oman | 128/421 |
| 4,928,706 | 5/1990 | Trick | 128/774 |
| 4,949,721 | 8/1990 | Toriu et al. | 128/421 |
| 4,962,766 | 10/1990 | Herzon | 128/741 |
| 4,977,895 | 12/1990 | Tannenbaum | 128/421 |
| 5,007,902 | 4/1991 | Witt | 604/117 |
| 5,020,542 | 6/1991 | Rossmann et al. | 128/741 |
| 5,092,344 | 3/1992 | Lee | 128/741 |
| 5,125,406 | 6/1992 | Goldstone et al. | 128/642 |
| 5,131,401 | 7/1992 | Westenskow et al. | 128/741 |
| 5,284,153 | 2/1994 | Raymond et al. | 128/741 |
| 5,284,154 | 2/1994 | Raymond et al. | 128/741 |
| 5,388,577 | 2/1995 | Hubbard | 128/639 |
| 5,388,578 | 2/1995 | Yomtov et al. | 128/642 |
| 5,411,025 | 5/1995 | Webster, Jr. | 128/642 |
| 5,560,372 | 10/1996 | Cory | 128/741 |

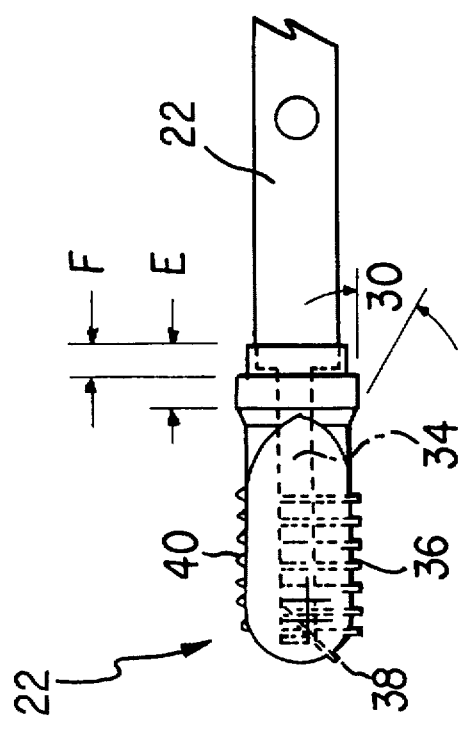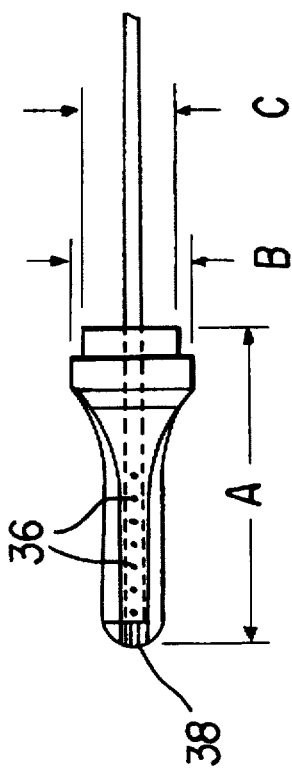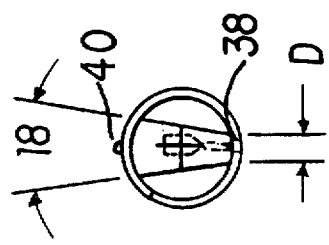

| LEVEL | TREND | SEQUENCE | RELATIVE LEVEL | ACCELERATION | STIMULUS |
|---|---|---|---|---|---|
| WELL BELOW BASELINE | RISING | WAS RISING, NOW RISING | AT RECENT MAXIMUM | ABOVE CRITERION | ON |
| BELOW BASELINE | STABLE | WAS RISING, NOW STABLE | AT RECENT MINIMUM | NEAR ZERO | OFF |
| AT BASELINE | FALLING | WAS RISING, NOW FALLING | ABOVE RECENT MAXIMUM | BELOW CRITERION | JUST STARTED |
| ABOVE BASELINE | | WAS STABLE, NOW RISING | BELOW RECENT MAXIMUM | WELL ABOVE CRITERION | JUST STOPPED |
| WELL ABOVE BASELINE | | WAS STABLE, NOW STABLE | ABOVE RECENT MINIMUM | | NEAR THRESHOLD INTENSITY (1) |
| | | WAS STABLE, NOW FALLING | BELOW RECENT MINIMUM | | MODERATE INTENSITY (2-3) |
| | | WAS FALLING, NOW RISING | | | STRONG INTENSITY (4-5) |
| | | WAS FALLING, NOW STABLE | | | HIGH INTENSITY (6-7) |
| | | WAS FALLING, NOW FALLING | | | NEAR MAX INTENSITY (8) |

APPARATUS AND METHOD FOR LOCATING A NERVE

BACKGROUND OF THE INVENTION

1. Field of the Invention

The present invention relates to an apparatus and method for stimulating and locating a nerve. More particularly, the present invention is an apparatus and method for precisely stimulating and locating a nerve using a closed-loop, automated system.

2. Related Art

Over the years, nerve stimulators have been used as a means to effectively locate peripheral nerves for surgical and therapeutic purposes. Such purposes include, for example, localization of the nerve for the administration of regional anesthesia or to avoid cutting the nerve during sectioning or excision of tissue. Nerve localization via the application of electrical energy is based on the fact that a pulse of electricity can stimulate a nerve fiber to contract an innervated muscle or cause paresthesia in the case of sensory nerves. It is known that if the site of stimulation is a significant distance from the target nerve, a stimulus of high intensity is required to effectively stimulate the nerve. If the site of stimulation is relatively close to the nerve, a low intensity stimulus is sufficient to stimulate the nerve.

Conventional nerve stimulators have taken the form of an insulated hypodermic needle coupled to a source of electrical current. To locate a nerve, the needle is placed within the tissue of the body in what is believed to be the vicinity of the nerve to be located. The needle is then manipulated by the operating physician, while simultaneously applying pulses of electrical current to the target area. Effective stimulation of the nerve is confirmed by visual detection of muscular contractions or by a report of paresthesia offered by the patient. Based on a subjective evaluation of the perceived effectiveness of each stimulus pulse, the operating physician repositions the needle and applies subsequent stimuli to the target area until localization of the nerve is achieved.

Some nerves are "complex" in nature because they are microscopic, include multiple branches, or are located within "messy" environments of the body. Such factors render localization of a nerve difficult to accomplish. Still other nerves evoke response patterns which may not be immediately detectable by visual observation alone and are, therefore, difficult to interpret by the operating physician. Stimulation of the cavernosal nerve, for example, results in 1) relaxation of the smooth muscles of the arterioles supplying the penis, 2) dilation of the arteries leading to the penis, 3) constriction of the veins carrying blood away from the penis, and, secondarily 4) accumulation of blood within the cavernosa. This type of response is especially difficult to evaluate because the response may not occur until some time after application of the stimulus. Indeed, measurable tumescence of the penis may not occur until two or more seconds following successful stimulation of the cavernosal nerve (if at all). Given the above-described factors, it is difficult for an operating physician to locate a nerve via visual inspection of the response pattern.

Nerve stimulators currently known in the art are dependent on the skill of the operating physician to 1) properly manipulate the stimulus applying means, 2) modify the intensity of the stimulus and 3) accurately assess the location of the target nerve based on an observation and interpretation of the elicited response.

Examples of two conventional nerve stimulators are disclosed in U.S. Pat. No. 3,682,162 to Coyler and U.S. Pat. No. 4,515,168 to Chester et al. The Coyler patent discloses a combined electrode and syringe needle which acts as a stimulation probe when the syringe needle is connected to an electrical supply. The Chester et al. patent discloses a nerve stimulator formed by clamping an electrode to the syringe portion of an anesthesia needle assembly. The device of the Chester patent includes a power supply, a pulse generating circuit, and a manually controlled current-adjusting potentiometer which allows the operator to manually adjust the current supplied to the stimulating needle.

Although both of the above-described devices may be used to stimulate a nerve, actual localization of the nerve is difficult, slow and imprecise because the operator is responsible for performing each step of the localization technique. That is, the operator must place the needle within the tissue of the body, deliver a stimulus to the tissue, watch for a response (or query the patient for a response in the case of a sensory nerve), interpret the response, reposition the needle, and apply a subsequent stimulus to the nerve. The devices of the Coyler and Chester patents are not provided with a means for detecting or interpreting successful stimulation of the target nerve, nor do they include a means for automatically varying the location of the stimulus site. Thus, the operator must be able to precisely move and hold the needle, as well as pay close attention to the associated muscle to avoid missing any contraction of the innervated muscle or other anatomical cue which may be indicative of successful nerve stimulation. Such a technique relies wholly on the skill of the operator and can be time consuming and inaccurate. If the operator inadvertently moves the stimulus applying means, misinterprets the response, or is not paying close attention to the surgical field, the nerve will not be accurately located. The skill of the operator is especially critical for localizing complex nerves (such as the cavernosal nerve) for the reasons discussed above.

Still another device for locating a motor nerve is disclosed in U.S. Pat. No. 2,704,064 to Fizzell et al. The Fizzell et al. patent discloses a neuromuscular stimulator having two probes for passing a current to a subcutaneous nerve. The probes are placed on the patient's body in the area of the nerve to be stimulated. As a current is passed to the probes, the operating surgeon watches for a response to stimulation of the nerve. If a response is observed, the surgeon assumes that the target nerve is within the vicinity of the stimulating probes.

While the device of the Fizzell et al. patent may be useful for the purpose of stimulating a nerve within a target area, precise localization of the nerve is not possible without close observation of the innervated muscle because the Fizzell device does not include an automatic response detection means. Like the Chester and Coyler patents, the operator of the Fizzell device must be capable of maintaining the stimulating probes in place to avoid slight movements in probe position which will affect the ability of the operator to accurately locate the nerve.

Still other devices attempt to stimulate a nerve at a sizeable distance therefrom using relatively large electrodes at high intensities (i.e., greater than 10 mA). Stimulation of a peripheral nerve at such an intensity is not useful for the purpose of refined localization of a nerve, as the response to such a stimulus may be so large (i.e., saturated) that subsequent movement of the electrode closer to the nerve (or farther from the nerve) yields no detectable change in the response. In order to determine the distance between the electrode and the nerve, the operator must be able to detect and interpret any change in the response to successful nerve stimulation.

In an effort to automate the technique for locating a nerve, Raymond et al. developed a device for automatically detecting and evaluating a response of a nerve to stimuli of varying intensity. Such a device is disclosed in U.S. Pat. Nos. 5,284,153 and 5,284,154 for use in localizing nerves for delivery of local anesthesia and for protecting nerves against inadvertent cutting during surgical procedures. The device of the Raymond et al. patents includes a stimulating probe or needle, a response detecting means, and a means for automatically modulating the intensity of subsequently applied stimuli so that the stimulating device ultimately converges to a stimulus intensity known to successfully stimulate the nerve when the probe is within a certain distance. While localization of single fiber nerves is efficient and rapid using the Raymond et al. device, it is difficult to locate multiple branches of a nerve or to locate nerves (such as autonomic nerves) having a long delay (greater than 1 second) between effective stimulation of the nerve and the onset of a detectable, measurable response. Furthermore, the response to stimulation of some visceral or autonomic nerves (such as the cavernosal nerve) may persist for several seconds after the cessation of successful stimulation. This delay and persistence of the response makes automated convergence to a predetermined stimulus intensity, as taught by the Raymond patents, slow (taking 20 seconds or more), as well as difficult to sustain since responses to small movements of the probe (which may effectively increase the distance between the probe and the nerve) will not be detectable until many seconds after the movement occurs. Thus, the ability of the operating surgeon to properly move and hold the stimulating probe at a particular location for a period of time is critical in order to successfully locate the nerve using the convergence method of the Raymond et al. patents.

With respect to nerve localization for surgical purposes, there remains a need for a device which is not dependent on the skill of the operator (i.e., automated) and is capable of taking into account the factors described above to enable the user to precisely and rapidly locate the target nerve using stimulating pulses of minimal intensities.

With respect to a method for locating a nerve (in particular, the cavernosal nerve) there is a need for a method which is capable of automatically locating a nerve using small electrodes at low stimulus intensities. Methods currently known to those skilled in the art utilize large single electrodes, multiple large electrodes disposed on a probe, or cuff electrodes at relatively high intensities (see e.g., Shafik, A., Cavernous Nerve Stimulation through an Extrapelvic Subpubic Approach: Role in Penile Erection, Eur Urol, Vol. 26, pp. 98–102, 1994 and Martin et al., Initiation of Erection and Semen Release by Rectal Probe Electrostimulation, *Journal of Urology*, Vol. 129, pp. 637–642, 1983.)

There is also a need for a method which is capable of automatically detecting and evaluating small changes in response patterns and of compensating for delay in the response to successful stimulation of the nerve. There is also a need to automate the movement between sites of stimulation. While the device of the Raymond et al. patents is capable of automatically detecting a response, there is no means for interpreting small changes in the response for the purpose of automatically modifying the site of subsequent stimulation.

In addition to locating nerves for surgical purposes, nerve stimulators have been found to be beneficial for therapeutic purposes. For example, stimulation of the cavernosal nerve (either transrectally or by an implant) has been envisioned as a treatment for impotence. Devices which have been developed for the purpose of stimulating the cavernosal nerve are disclosed, for example, in U.S. Pat. No. 3,941,136 to Bucalo, U.S. Pat. No. 4,124,028 to Gallo, and U.S. Pat. No. 4,663,102 to Brenman et al. Although all of the afore-mentioned patents disclose devices which are capable of delivering a stimulus to innervated body tissue, none disclose an apparatus and method which precisely and automatically locate a nerve for optimal stimulation thereof.

The Brenman patent, in particular, discloses a stimulating device which is inserted into the rectum of the patient to a stimulate penile erection. The device includes electrical circuitry for generating an electrical signal to be applied to the pelvic nerve. Electrodes, placed at specific locations on the surface of the device, apply the signal to the patient. At least one of the electrodes closely contacts the prostate gland when the device is operatively disposed at a region or spot on the prostate gland previously determined to be sensitive to electrical stimulation. Identification of the spot or spots to be stimulated by the device is accomplished by a separate, glove-like apparatus which includes a plurality of electrodes mounted thereon. After selecting the desired stimulation site or sites with the glove, the stimulating electrodes are positioned on the device (in accordance with the electrode positioning of the glove) so that the electrodes contact the "hot spots" when the device is positioned within the rectum.

Identification of the hot spots via the Brenman device may be inaccurate, however, in light of the fact that the physician is responsible for manipulating the glove-like device and for visually detecting and monitoring the tumescence response (i.e. the Brenman device is not an automated, closed-loop system). Because the Brenman device is not automated, it is not capable of taking into account the afore-described factors of the cavernosal nerve system, including the delay which occurs between successful stimulation of the cavernosal nerve and the onset of tumescence. Moreover, it would appear that accurate placement of the electrodes on the stimulating device is difficult since identification of the hot spots is accomplished using a separate, glove-like apparatus which is structurally different than the device. Finally, should the rectal tissue shift, the Brenman device provides no means to confirm that the electrodes of the device are still optimally aligned with the hot spots of the prostate.

Still other devices for treatment of impotence (such as the Gallo device, for example) utilize especially large electrodes which stimulate the tissues of the body at high intensities. As stated above with respect to nerve localization for surgical purposes, stimulation of the nerve at a high intensity may result in a saturated response which is difficult to interpret for the purpose of determining the location of the stimulus applying means with respect to the pelvic nerve. In addition, a high intensity stimulus by a large electrode produces a diffuse spread of electrical current that may stimulate a nerve other than (or in addition to) the target nerve and which may reduce the user's ability to stimulate the target nerve. Furthermore, stimulation at high intensities is known to cause the subject considerable pain and discomfort.

Large electrodes are inappropriate either for maximizing a response or for localizing a nerve. The current density is dissipated by the large area of the electrode, making local nerve stimulation more difficult (for constant current source stimulation). In the case of voltage source stimulation, an exceedingly high level of net energy is applied to the tissue of the body via a large surface electrode. Indeed, the energy may reach the point of actually heating tissue to dangerous levels.

Thus, for therapeutic treatment there is a need for a nerve stimulating and locating device which is not dependent on the skill of the user and is capable of precise location by taking into account the factors of an autonomic nerve system. A device which is capable of stimulating a nerve at low intensities to decrease or altogether avoid patient discomfort is also desired.

SUMMARY OF THE INVENTION

It was with the above-described needs in mind that the present invention was developed. In light of the fact that successful localization of the target nerve is dependent upon the skill of the operator, and more particularly on the position of the probe, it has been envisioned that stimulation of the nerve by a means which automatically varies the site of stimulation may be more effective than stimulation by a single, physically manipulated electrode. This is particularly true where the nerve fibers are distributed over an area such that a single electrode cannot effectively stimulate the entire nerve bundle. Accordingly, the present invention is an apparatus and method for locating and stimulating a nerve at specific stimulus parameters which are known to stimulate the nerve when the stimulus is applied to the nerve within a certain distance. In the preferred embodiment of the invention, the site of stimulation is electronically "floated" over the target area by an array of stimulating electrodes. Activation of the array is governed in accordance with an electrode selecting algorithm which automatically interprets and evaluates the response of the nerve to successful stimulation to determine which electrodes are successfully stimulating the nerve. Because each step of the locating method is automatically controlled, the skill of the operator is no longer as important a factor in successful nerve localization. In this sense, the apparatus and method of the present invention is closed loop.

In one aspect of the invention, the apparatus for locating and stimulating a nerve includes a means for applying a stimulus to a nerve at a plurality of sites, a means for detecting a response to a stimulus, and a means for automatically modifying the site of stimulation. The means for automatically modifying the site of stimulation includes a means for interpreting the response provided by the response detecting means. The means for applying a stimulus to a nerve may be an array of stimulating electrodes, a magnetic induction device, or an electrode movably positioned on a track. The electrodes of the array may be arranged in a multi-dimensional configuration for activation in successive triplets to determine the longitudinal axis and symmetry of the nerve. The interpreting means interprets data from the response detection means to discriminate between trends in response states corresponding to periods of successful stimulation and states corresponding to unsuccessful stimulation of the nerve.

In another aspect of the invention, an apparatus for stimulating and locating the cavernosal nerve is provided. The apparatus includes a probe having an array of electrodes, a control means for governing activation of the array of electrodes, and a response detection means for detecting and measuring a tumescence response. The electrodes of the array are activated in accordance with an electrode selecting algorithm which evaluates a tumescence response to successful stimulation of the cavernosal nerve. The response detection means provides response feedback information to the control means for evaluation by the electrode selecting algorithm. A tumescence monitor comprising a mercury-filled distensible tubing may serve as the response detection means. The apparatus may also include a filter to isolate changes in the tumescence response from changes induced by other aspects of the locating or surgical procedure. If desired, the most distal electrode of the array may be angled at approximately 45° to position the electrode at the physical tip of the array, thus allowing the array to function as a single electrode or pointer. The apparatus may also include a means for indicating to the user the location of the nerve to the user.

In another aspect, the invention is an apparatus for locating and optimally stimulating a nerve for therapeutic purposes. The apparatus includes an implant comprising an array of electrodes, a control means for governing activation of the array, and a response detection means. The control means of the apparatus activates the electrodes of the implant in accordance with an electrode selecting algorithm which evaluates a response to successful stimulation of the nerve. The response detection means of the apparatus provides response feedback information to the control means for evaluation by the electrode selecting algorithm. The implant may take the form of a stent which is implanted within a natural body cavity of the patient. The response detection means, particularly for cavernosal nerve stimulation, may be a tumescence monitor.

In yet another aspect of the invention, a method for stimulating and locating a nerve is provided. The method includes the steps of applying a stimulus to a nerve, detecting a response to stimulation of the nerve, evaluating the response to stimulation of the nerve, and automatically modifying the site of stimulation based on the evaluation of the response. The stimulus is of an intensity known to stimulate the nerve when the site of stimulation is within a known distance from the nerve. The site of stimulation is modified in accordance with a site selecting algorithm which is based on information provided by a response detecting means and a stimulation input means.

A method for specifically locating the cavernosal nerve is also provided. The method includes the steps of applying a stimulus to the nerve to evoke a tumescence response, detecting a tumescence response to stimulation of the nerve, evaluating the tumescence response to the stimulation of the nerve, and automatically modifying the site of subsequent stimulation based on an evaluation of the tumescence response. The stimulus is of an intensity known to stimulate the nerve when the site of stimulation is within a known distance from the nerve, specifically 1 mm. The steps of the method are repeated until localization of the nerve is achieved. The stimulus may be a train of electrical pulses. A tumescence monitor may be used to detect a response to successful stimulation of the nerve. The change in the response pattern may be evaluated by a response interpreting means. The site of stimulation may be automatically modified in accordance with an electrode selecting algorithm.

In still another aspect of the invention, a method for stimulating the cavernosal nerve to facilitate localization thereof is provided. This method includes the step of applying a stimulus to a nerve which is capable of initiating sub-maximal tumescence of the penis such that subsequent tumescence responses to subsequently applied stimuli occur with shorter delay from the onset of successful stimulation. The stimulus may be electrically, chemically, or mechanically applied to the patient.

BRIEF DESCRIPTION OF THE DRAWINGS

Various objects, features and attendant advantages of the present invention will be more fully appreciated as the same becomes better understood from the following detailed description of the present invention when considered in connection with the accompanying drawings, in which:

FIG. 3A is a side elevational view of the array tip shown in FIG. 2;

FIG. 3B is a bottom plan view thereof;

FIG. 3C is a front elevational view thereof;

FIG. 9 is a chart of a library of states or characteristics of a response;

DETAILED DESCRIPTION OF THE INVENTION

With reference now to the attached Figures, the apparatus and method of the preferred embodiment of the invention will be described.

Apparatus of the Invention

Figure 1:
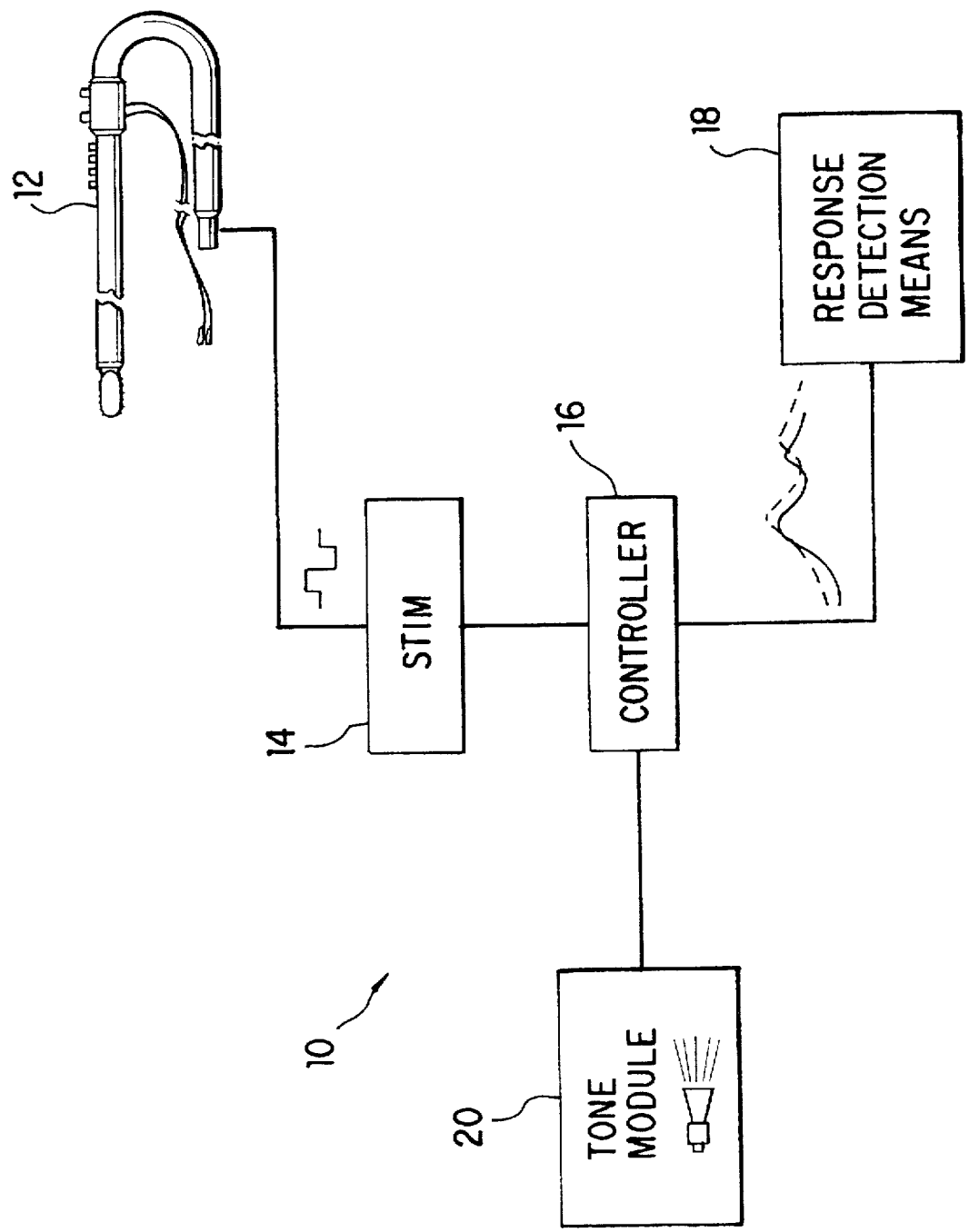
FIG. 1 is a schematic drawing of the component parts of the apparatus of the present invention.

Turning now to FIG. 1, a preferred embodiment of the apparatus for locating a nerve is shown generally at 10. Nerve locator 10 generally comprises a stimulating probe 12, a stimulator circuit 14, a control means 16, and a response detection means 18.

As shown in FIGS. 1, 2 and 3A-3C, stimulating probe 12 is generally wand-like in shape and includes a tip portion 22, a flexible handle 24, a switch panel 26, a flexible cable 28 and a connector 30.

Tip portion 22 is curvilinear in shape and extends approximately 0.760 inches from distal end 32 of handle 24. Tip portion 22 is provided with a pc board 34 to which an array of stimulating electrodes 36 are connected in a linear relationship. A polycarbonate, or other suitable medical grade plastic, is molded about the pc board and electrode array to form the main body element of the tip portion of the probe.

Electrodes 36 are preferably platinum having a diameter of approximately 200-500 microns. The electrodes should be no smaller than the described dimension, as a protruding electrode of a smaller diameter may cut or otherwise damage the nerve. Electrodes 36 extend approximately 0.1-0.75 mm from the main body portion of the probe so that the tips of the electrodes may be brought into contact with the tissue to be stimulated. As shown in FIGS. 3A-3C, eight electrodes are positioned on pc board 34 approximately 1.0 mm apart. Although eight electrodes are shown, it should be realized by those skilled in the art that any number of electrodes may be positioned on the pc board at any suitable distance. Naturally, the spacing and number of the electrodes may be varied depending on the type of nerve to be stimulated and the tissue of the target area. For example, 4-50 electrodes may be positioned on the pc board at a distance ranging between approximately 0.1-4.00 mm. Furthermore, the length of electrodes 36 may be varied for the purpose of locating a nerve which is deep within the tissues of the body.

In the preferred embodiment, the most distal electrode of the array 38 is arranged approximately 45° off the line of the other electrodes so that the tip of the electrode may be used as a pointer or as a means to more accurately position the array of the probe within or beneath the tissues of the body. In an alternative application of the invention, stimulation may be restricted to the most distal electrode of the array for use as a single, manually-moveable electrode assembly.

The electrode arrangement illustrated in FIGS. 1, 2, and 3A-3C is especially advantageous for localization of the cavernosal nerve, as the most distal electrode of the array may be directly placed beneath the prostate and below the urethra. Naturally, more than one electrode may be offset at any angle to facilitate positioning of the probe in any desired area. Similarly, the tip portion of the probe may be otherwise contoured to allow the tip portion of the probe to conform to the surface area of the tissue to be stimulated. It is also envisioned that the tip portion of the probe may be formed from a plastic which is capable of closely conforming to the surface area of the tissue to be stimulated.

The preferred dimensions of the tip portion of the probe are listed below (in inches) as identified in FIGS. 3A, 3B, and 3C of the drawings:

| | |
|---|---|
| Length A | .760 |
| Diameter B | .300 |
| Diameter C | .238 |
| Width D | .070 |
| Width B | .150 |
| Width F | .075 |

Naturally, the tip portion of the probe may be otherwise dimensioned in accordance with the type of nerve to be located and its location within the tissue of the human body.

Correspondingly positioned above each electrode is a small light emitting diode (LED) 40 which indicates to the user which electrode has successfully located the target nerve (that is, under which electrode(s) the target nerve, or branches thereof, lies). Each LED is approximately 1 mm in diameter and corresponds in location to the spacing of the electrodes. If the nerve to be located is in a "messy" surgical environment (that is, if there is a lot of blood or other bodily fluids/tissues in the surgical field), the operator may not be able to visualize the LED array of the device. It is, therefore, desirable to provide a second array 25 (FIG. 2) along the handle portion of the probe to enable the operator to see which electrode has successfully located the target nerve.

At its proximal end 32, tip portion 22 of probe 12 is joined to a handle 24 which enables the user to properly position the probe within the body tissue. Handle 24 is made malleable by providing a copper wire 48 of 8-12 gauge through the central core of the handle. Handle 24 is preferably formed from any suitable medical grade plastic which exhibits a certain degree of flexibility and is capable of being sterilized.

Formed integral with handle 24 is a panel 26 which includes switches 44 and 46 for initiating and terminating the various stimulating modes of the apparatus. Extending from panel 26 is a patient ground lead 50. Electrodes 36 are preferably grounded to a stainless steel spreader plate used to maintain the tissue of the patient in an exposed condition for surgical purposes. If a spreader plate is not available, the ground can be clipped to a silver plate or other implement with a large surface area in contact with any wet body tissue, and preferably axial to the course of the nerve to be stimulated.

A suction port 33 (FIG. 2) formed within handle 24 is provided to remove bodily fluids from the surgical field which may interfere with the surgeon's ability to view the surgical field.

At the end opposite handle 24, switch panel 26 is connected to a silicone jacketed, flexible cable 28 which is approximately 12 ft. in length to lend the operating surgeon an optimum range of movement. A cable similar to that for use with an electrocautery probe is suitable for the purposes of the present invention.

Molded on the end of cable 28 is a suitable 9-wire connector 30 for coupling the probe of the apparatus to the control means of the invention. Such a connector is available from Lemo, Basil, Switzerland.

Stimulator circuit 14 generates a symmetric biphasic square pulse current in response to a trigger by control means 16. The circuit initially converts a digital number to a voltage level between 0–5 volts. An inverting unity gain circuit transforms this single voltage level into two symmetric levels, one positive and one negative each having a matching amplitude. The digital to analog convertor voltage is varied by program control between 0–5 volts. A standard timing board (such as the CTM φ5 available from Keithley Metrabyte, Taunton, Mass.) is used under program control to control a silicon switch (e.g., a DG 300, siliconix, or like switch) to connect first the negative and then the positive voltage to a summing operational amplifier (op-amp) "adder", thus forming a biphasic voltage pulse whose amplitude is governed by the DAC voltage and whose timing and duration of each phase is governed by the two pulses from the timing card. The two pulses are separated by 1 μs such that the two phases of the biphasic voltage pulse combine separately at the output of the adder. A voltage-controlled current generator using op-amp driving high voltage current mirrors connected to high voltage batteries converts this biphasic voltage signal to a pulse of constant current which is deliverable to the target area by stimulating probe 12. The current pulse ranges from 100 μs–1000 μs in the duration of each half pulse and in amplitude from ±200 μA to ±25 mA. The delivery of such pulses to particular electrodes of array 36 is accomplished by a set of relays actuated under program control. It should be noted that the stimulus generated by stimulator circuit 14 may be in isolated pulses or in sustained trains of either regularly timed or irregularly timed pulses. Thus, a single stimulus may comprise a single pulse or a train of multiple pulses. The importance of a pulsed stimulus viz-a-viz a continuous stimulus will be described in more detail below.

Control means 16 comprises a computer which utilizes data acquisition hardware and software. An Intel 80386 DX computer and a Metabyte-16 data acquisition board (available from Metabyte Corporation, Taunton, Mass.) are suitable for the purposes of the present invention. The data acquisition board should have at least a one channel (12 bit) analog-digital converter, one or two digital-analog converters, and timer chips. The data acquisition software is written to interpret a response from response detection means 18 (to be described in more detail below) in accordance with a response interpreting and electrode selecting algorithm. The response interpreting and electrode selecting algorithm of the control means is a function of the nerve to be located and is based on empirical data. The algorithm is premised on response pattern recognition and may take into account many factors, including the multiple phases in the response pattern of an autonomic nerve, the delay between successful stimulation of the nerve and the onset of a detectable response, and the stimulation and response history of the nerve. This information is used to formulate a response interpreting algorithm which determines whether a particular electrode of the array has successfully stimulated the nerve.

The response interpreting algorithm is based on a library of response states derived from empirical data. This library of states may be categorized as shown in FIG. 9. The listing of states detailed in FIG. 9 is a representation of some of the possible conditions or characteristics of any given response. The "level" of the response is characterized with respect to a pre-determined baseline value for the particular nerve to be located. The response interpreting algorithm determines whether the response is above baseline, at baseline, below baseline or a gradation thereof.

The response "trend" is evaluated in light of the direction of the previous level of the response. That is, the algorithm determines whether the response is rising, stable or falling in comparison to the previous level of the response.

The "relative level" of the response is also evaluated with respect to the previous response level. For example, the algorithm considers whether the response is greater than or less than a recent maximum response. There is an implied variable in the "relative position" with respect to a time interval which may be defined by 2 epochs timed at 20 and 5 seconds, for example.

Each response includes an "acceleration" property which is indicative of the rate of change of the response. This characteristic is evaluated against a predetermined criterion value of acceleration and is based on a time interval which may be evaluated, for example, every 5 seconds.

The "stimulus" state is indicative of whether the stimulus is on, off, recently applied, or recently stopped for that response record.

Each response is evaluated and characterized at a time, t, as set forth above. For example, the level of the response may be above baseline, rising at a rate of change greater than criterion, and positioned relative to a recent maximum. For each combination of states, the algorithm will determine whether the response is indicative of successful or unsuccessful stimulation of the nerve. After categorizing the response, the algorithm works backwards (taking into account the delay factor) to determine which electrode or electrodes were responsible for successfully stimulating the nerve. Based on this evaluation, the electrode selecting algorithm of the control means sets up a subsequent stimulus train among that subset of electrodes. Ongoing stimulation of the target nerve is restricted (as governed by the algorithm) to a subset of the array which produces a criterion response with the least magnitude of stimulation. The algorithm continues to interpret the response to successful (as well as unsuccessful) stimulation of the nerve until the location of the electrode(s) closest to the nerve is identified. Upon locating the nerve, the LED(s) corresponding to the electrode lying immediately above or adjacent to the target nerve (or branches thereof) is illuminated to indicate to the operator the location of the target nerve beneath the array.

In another embodiment of the invention, control means 16 may be provided with a separate indicator program which audibly indicates to the user that the target nerve has been located. Localization is indicated to the user via a tone module 20 of constant or variable pitch.

With reference again to FIG. 1. the response detection means of the present invention will now be described. As shown in the schematic of FIG. 1. response detection means 18 is shown connected to control means 16 of the device. Response detection means 18 functions to detect and measure a response to successful stimulation of the target nerve. The magnitude of the response is recorded by the response detection means and forwarded to control means 16 for interpretation by the algorithm of the device. Control means 16 interprets the response data provided by response detection means 18 in order to determine which electrode or electrodes of the array were responsible for successful stimulation of the target nerve. The response data is evaluated by the algorithm in accordance with the stimulation and response history of the nerve and the other factors discussed above which tend to complicate localization of the target nerve. As the response information is received and interpreted. the electrode selecting algorithm of the invention determines which subset of electrodes will receive the next stimulation pulse. The device continues to stimulate the nerve (and interpret the response thereto) until localization of the target nerve is achieved.

Figure 4:
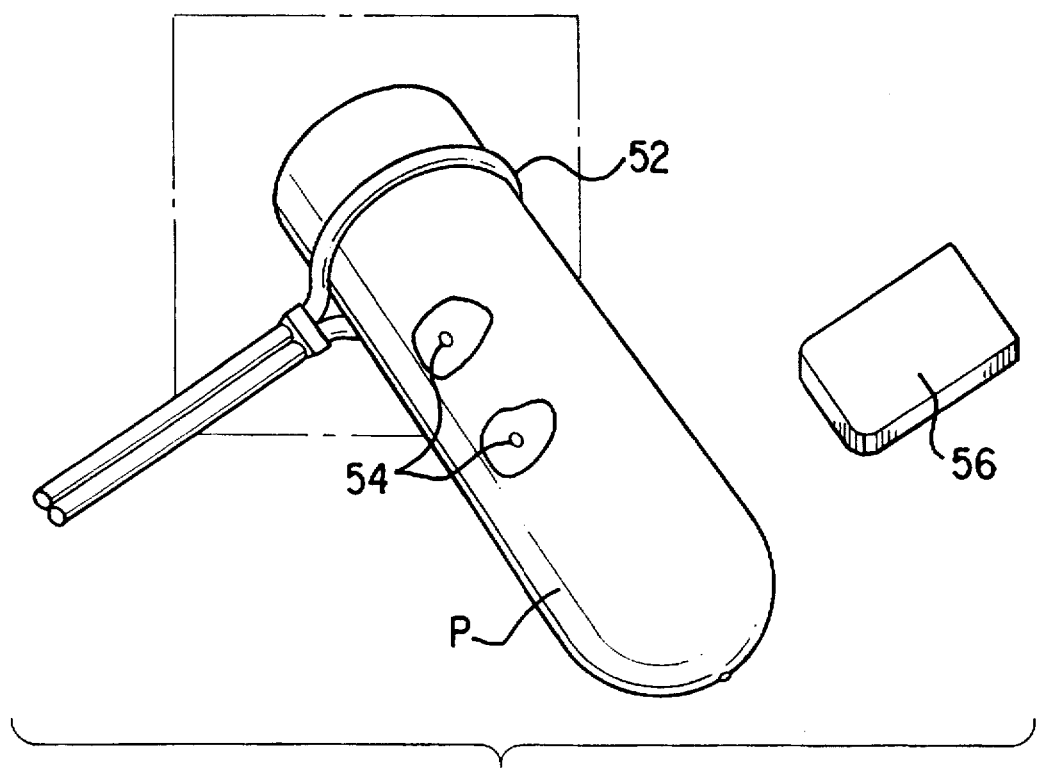
FIG. 4 illustrates several devices for use as the response detection means of the invention.

Selection of a device to detect and measure a response to successful stimulation is dependent upon the nerve to be located. For example. if the user is attempting to locate a sensory nerve, any means capable of detecting and measuring action potentials within a nerve fiber may be used to accomplish the objectives of the invention. For motor nerves, any means capable of detecting and measuring a response of the innervated muscle or organ is suitable. For the cavernosal nerve. in particular, any means capable of detecting and measuring tumescence of the penis (or dilation of cavernosal blood vessels, or other direct results of stimulation of the cavernosal nerve) may be used to enable localization of the nerve. Devices capable of detecting and measuring penile tumescence are disclosed in FIG. 4. Such devices include distensible tubing 52 filled with a conductive fluid (such as mercury). EMG electrodes 54. and a Doppler flow head 56 which is positioned on the dorsal artery of the penis P to image the same. If EMG electrodes are used, an amplifier must be incorporated into the device to boost the detected signals to levels appropriate for analog-digital conversion by control means 16. A laser Doppler flow head (not shown) for measuring capillary flow within the tissue of the penis may also be used. Increases (or decreases) in tumescence may be also be detected by a needle capable of detecting changes in pressure within the spaces of the erectile tissues of the penis. Still other devices for measuring tumescence include a condom or sheath-like device which is capable of detecting changes in resistance as the volume of blood within the penis changes. It is also envisioned that tumescence may be measured in terms of tissue density by an ultrasonic apparatus. Naturally, other devices capable of detecting and measuring a response to successful stimulation are suitable for accomplishing the objectives of the present invention.

In the preferred embodiment of the invention, a non-linear filter to eliminate noise from a surgical knife (or noise from other irrelevant surgical intervention) is provided to assist in the detection of the very earliest signs of effective stimulation. Other filters for optimally enhancing signals are used in the signal detection circuits of the response detecting means.

Figure 10:
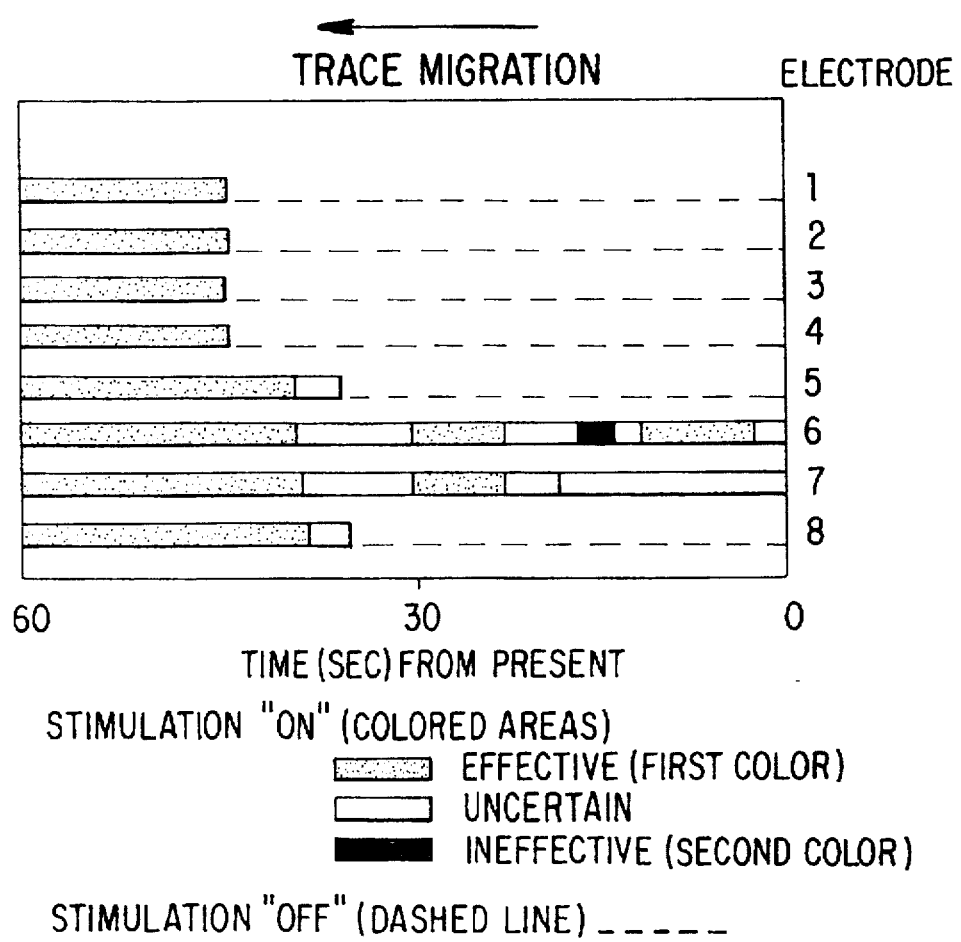
FIG. 10 is an illustration of a gauge comprising a plurality of linearly arranged LEDs for communicating stimulation information to the operating physician.

With reference to FIG. 10. it is envisioned that the apparatus of the invention may be provided with a separate gauge consisting of a plurality of linearly arranged LEDs which may be illuminated to communicate stimulation information to the operating physician. For example. the left end of the gauge could be illuminated (as dictated by the control means of the apparatus) to indicate to the physician that the last successful stimulation epoch occurred 60 seconds ago. The middle portion of the gauge could be illuminated to indicate that the last successful epoch occurred 30 seconds ago. while the right-hand end of the gauge could be illuminated to indicate that successful stimulation occurred 1 second ago. Naturally, the gauge may be provided with any number of LEDs and may be illuminated to communicate any type of information concerning stimulation of the nerve. It is also contemplated that the LEDs of the gauge may be colorized to reflect effective (or ineffective) stimulation of the nerve.

Operation of the Apparatus of the Invention

Having described its component parts, operation of the apparatus will now be described.

Priming

For certain types of nerves (such as the complex, autonomic nerve described above), it has been found that "preconditioning" or "priming" of the nerve assists in localization in a more precise and expeditious manner by disposing the system to respond more quickly and to a greater degree to a subsequently applied stimulus. As noted earlier in this application, autonomic nerves (such as the cavernosal nerve) may be characterized by the fact that there is a time delay between successful stimulation of the target nerve and the onset of a detectable response (that is, the response of an innervated muscle or organ does not immediately follow successful stimulation of the nerve). The results of recent studies indicate that this time delay may be decreased by applying "priming" stimuli of sub-saturation intensity to the target nerve. As stimuli of such an intensity are applied to the target nerve, the response of the associated muscle or organ is evoked more rapidly and to a larger magnitude when subsequent stimuli are delivered within an appropriate delay (2–60 sec) from the priming stimuli. This decrease in the time delay assists in localization of the nerve, as each change in the response (i.e. the differential response) of the associated muscle or organ may be more quickly and precisely tied to a particular electrode or stimulation site. Evidence of the existence of the priming phenomenon will be discussed in more detail below with particular reference to localization of the cavernosal nerve.

To prime the target nerve, the operator places the electrode array of probe 12 on or near an area believed to contain the target nerve. The operator then activates the priming switch located on handle 24 of probe 12 to initiate the priming mode of the apparatus. Upon activating the priming switch, control means 16 initiates a stimulation pattern or sequence using either all or a subset of the electrodes of the array. The intensity of the stimulus train to be applied to the nerve generally ranges between 2–10 mA. 100–800 μs. 5–30 Hz and is dependent on the type of nerve to be primed. That is, the software which governs the priming mode of the apparatus is based on a database of information which is specifically directed to effective stimulation of the target nerve at various stimulating intensities and distances. Thus, for the priming mode of the invention, the control means prescribes a stimulating sequence of a constant or variable intensity which has been previously determined to evoke a sub-saturation response for the type of nerve to be located.

Control means 16 continues to run the pre-defined priming sequence without stopping to actually locate the nerve. The control means never stops to consider which electrode is successfully stimulating the nerve, but continues to run the same sequence to record stimulation information for use during the locating phase of the invention. In this respect, the priming phase of the invention is "open-loop" in that the control means does not evaluate or interpret the response of the nerve for the purpose of locating the same with respect to the electrodes of the array. Sufficient priming of the nerve is achieved when tumescence of approximately 10–20% of the maximum tumescence has been achieved.

It should be noted that priming of the target nerve may also be accomplished by using a single electrode of the array at a sub-saturation intensity. Regardless of the number of stimulating electrodes to be used, the application of stimuli of a sub-saturation intensity will serve to prime the nerve for the purpose of decreasing the time delay between effective stimulation and the onset of a measurable response.

Although priming of a nerve has been described using stimulating pulses of electricity, it should be noted that priming of a nerve may also be achieved chemically or mechanically. For example, the patient may be injected with a drug known to evoke a desired response from a muscle or organ innervated by the target nerve. To achieve a penile erection, for example, the patient may be injected with papaverine for the purpose of priming the cavernosal nerve. Alternatively, the nerve may be stimulated mechanically by a applying a vibrating pulse to an appropriate area of the patient.

While the priming step of the invention facilitates rapid and precise localization of the target nerve, it should be noted that priming is not required to successfully locate the nerve. The algorithm of the invention will result in localization of the nerve whether or not the priming step is performed.

Locating

Following priming, the device is switched to the locating mode to actually locate the nerve. At this stage, the apparatus of the invention is "closed-loop" in nature in that the control means interprets a change in the response pattern for the purpose of determining which electrode of the array is responsible for stimulating the target nerve. This operation is independent of the operator and is therefore more accurate and precise than previously known nerve locators which are dependent on the skill of the operator to manipulate the device and interpret response feedback information.

Upon activating the locating switch of the apparatus, the electrode selecting algorithm of the control means initiates a pre-arranged sequence among all or part of the array. It should be understood that the electrodes of the array may be fired in any particular order or sequence.

The stimulus pulses of the locating phase are of an intensity capable of effective stimulation of the target nerve when applied within a distance of 1–2 mm. As the electrodes are fired in the pre-arranged sequence, the response detecting means of the apparatus detects and measures a change in the response of the associated muscle or organ. A response to successful stimulation of the target nerve will rapidly occur, as the priming step of the method has effectively decreased the time delay between effective stimulation of the nerve and the onset of a measurable response. Response feedback information from the response detecting means is sent to the control means for interpretation by the response interpreting algorithm. The response interpreting means compares the absence of a change in the response at one (or more) sites against a change in the response at one or more other sites. Based on this comparison, the control means (via electrode selecting algorithm) determines which electrodes were most successful in stimulating the target nerve (that is, which electrodes evoked a response indicative of successful stimulation of the nerve). Equally important, those electrodes which were not responsible for evoking a change in the response pattern will be identified.

The electrode selecting algorithm of the control means restricts a second stimulating sequence to that set of electrodes known to evoke a response to successful stimulation of the target nerve. The response to the second sequence is evaluated by the control means to further determine the position of the nerve beneath the electrode array. Based on the stimulation and response history derived from the first and second sequence, the control means prescribes a third sequence. The program continues to run until the most effective (i.e., closest) electrode(s) is identified. The electrode(s) closest to the nerve has been determined to be that electrode capable of evoking a change in the response pattern at the lowest intensity known to evoke a response when the electrode is within 1 mm of the target nerve.

Upon identifying the most effective electrode(s), the LED(s) corresponding to that electrode is illuminated on the probe tip and on the handle portion of the probe. At this point, the stimulus pulse may be further decreased to approximately 0.5 mA to confirm that the target nerve is indeed beneath the marked electrode(s).

It should be noted that throughout the locating phase, the intensity of the stimulus need not be changed in response to effective stimulation of the nerve. The fixed stimulus intensity selected for the locating phase is capable of locating the nerve when the stimulating probe is within 1 to 2 mm of the target nerve. It should be further realized that, like the priming phase, the electrodes of the array may be fired in any order (in either direction) and are not necessarily fired in sequentially adjacent order.

Application of the Apparatus and Method of the Present Invention for Locating the Cavernosal Nerve It has been found that during radical prostatectomy surgery, the ability of the operating surgeon to locate and spare the cavernosal nerve greatly reduces the otherwise high, post surgery rate of impotence. The apparatus and method of the present invention is especially suited for locating the cavernosal nerve, as it is capable of taking into account the response pattern which is evoked by successful stimulation of the cavernosal nerve. The operation of the device with respect to localization of the cavernosal nerve will now be described.

Evidence of the Effectiveness of Priming the Cavernosal Nerve

For the cavernosal nerve, it is known that there is a time delay between effective stimulation of the nerve and the onset of a change in tumescence. In humans, this delay may be as short as 2 seconds and as long as 30 seconds. Based on experimental studies performed on dogs and rats, it has been discovered that sustained stimulation at a sub-maximal intensity will minimize the response delay to a subsequently applied stimulus train.

Figure 5A:
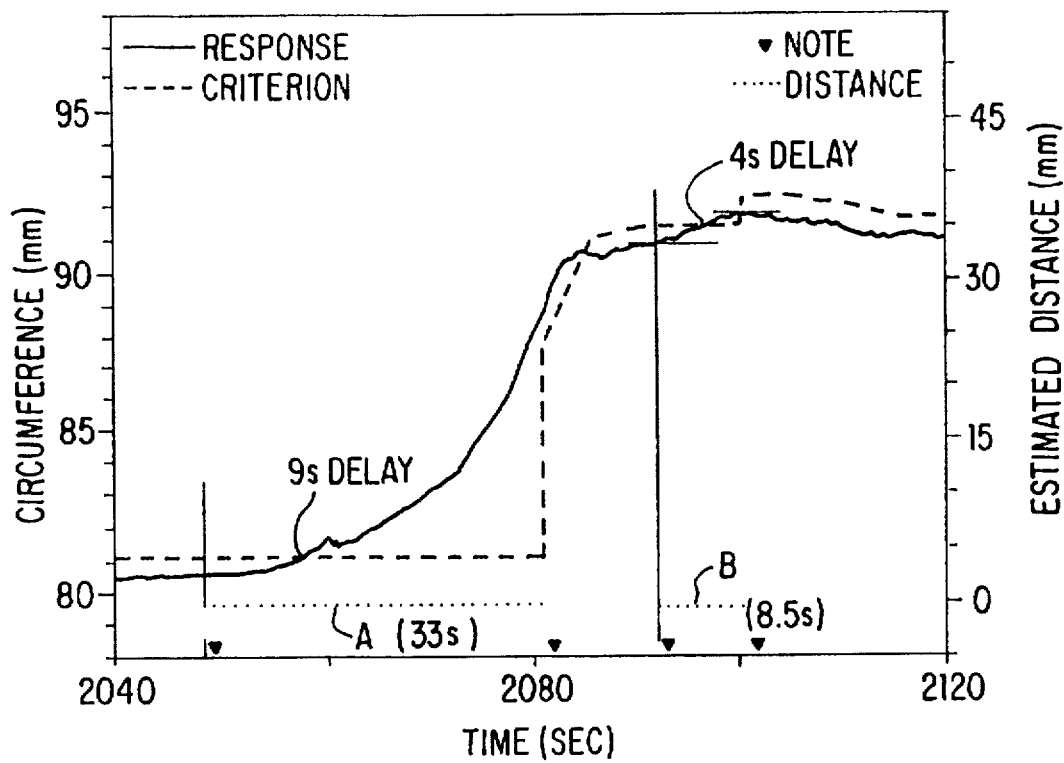
FIGS. 5A-5C illustrate the latency phenomenon as detected by a six-minute stimulation epoch in a canine preparation.
Figure 5B:
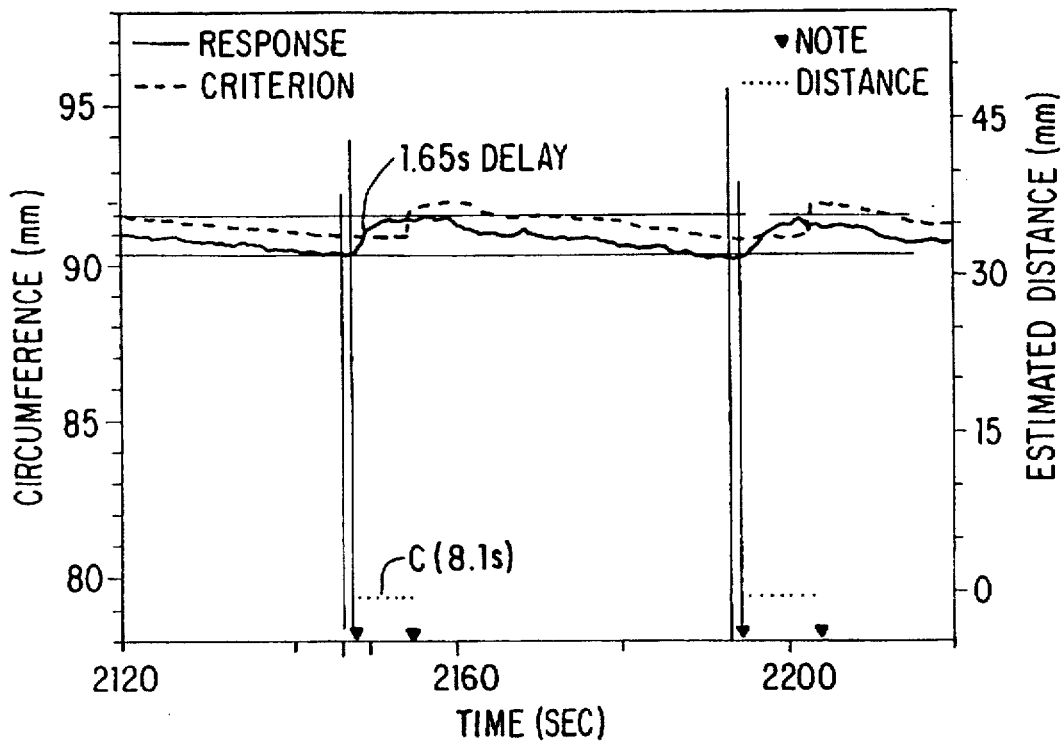
Figure 5C:
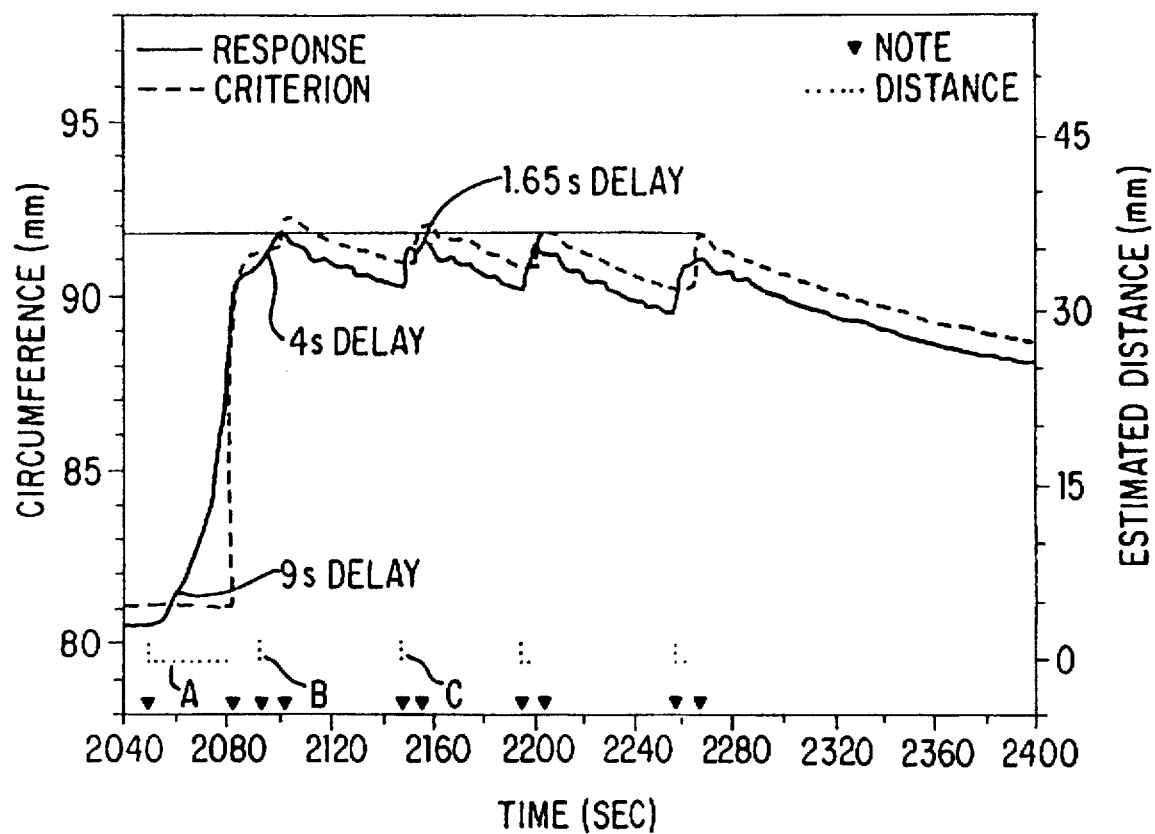

Evidence of the effectiveness of priming for the cavernosal nerve is illustrated graphically in FIGS. 5A–5C. FIG. 5A illustrates a first and second stimulus epoch of a six-minute canine record, while FIG. 5B illustrates a third and fourth stimulus epoch of the same record. FIG. 5C is a summation of the graphs of FIGS. 5A and 5B. As seen in FIG. 5A, a first stimulus epoch A was applied to the subject dog at time 2044 for a total of 33 seconds. The parameters of the stimulating probe were standardized at a level sufficient to stimulate the nerve within a distance of 1–2 mm (i.e., 8 mA, 800 µs, 16 Hz). Although the stimulus epoch was initiated at time 2044, the response of the nerve did not pass criterion until time 2053, a full 9 seconds after the onset of the initial stimulus epoch. Thus, for the first stimulation epoch, a 9 second delay between stimulation and an increase in tumescence was observed. The second stimulus epoch B was initiated at time 2092 for a total of 8.5 seconds. During the second stimulus epoch, the response of the nerve passed the criterion level at approximately time 2096, a total of 4 seconds after the onset of the second stimulus epoch. The third stimulus epoch C (see FIG. 5B) was initiated at time 2147 for 8.1 seconds. After only 1.65 seconds, the response of the nerve exceeded the criterion level. Thus, it can be seen that by priming the cavernosal nerve, the time delay between effective stimulation and the onset of a response change may be decreased to about 1–2 seconds.

Figure 6:
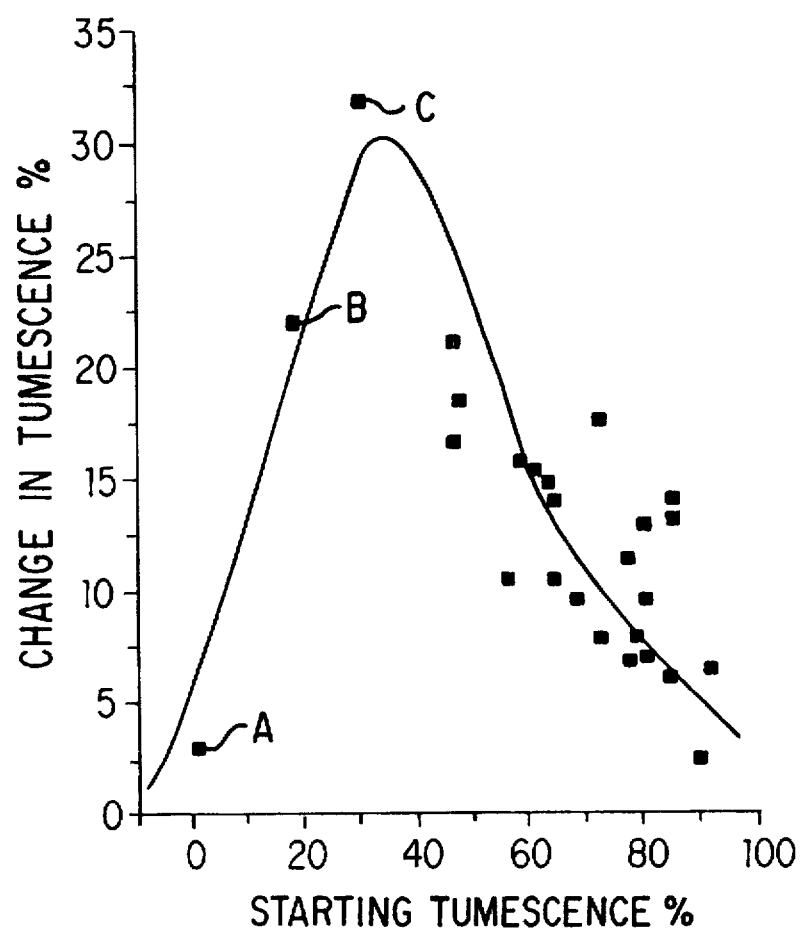
FIG. 6 is a plotting illustrating the change of tumescence versus starting tumescence.

Yet another illustration of the effectiveness of priming is shown in FIG. 6. FIG. 6 plots the results of one priming study from an experiment on 7 dogs. It can be seen that at a starting tumescence of 0% (no priming), stimulation of the cavernosal nerve yields only a 4% percent change in tumescence (point A). However, when starting tumescence is at 20% (moderate priming), a 22.5% change in tumescence is observed (point B). At a starting tumescence of 30%, a significant 32% change in tumescence occurs (point C).

Taken together the graphs and plot of FIGS. 5 and 6 illustrate that after sufficiently stimulating the cavernosal nerve to elicit at least a partial tumescence response, a measurable change in the tumescence response occurs more rapidly and on a larger magnitude to subsequently applied stimulus pulses delivered to the nerve before the response fully recovers.

Priming of the cavernosal nerve may be accomplished with the array probe of the present invention or with a single stimulating electrode. Regardless of the number of electrodes to be used, the priming method for the cavernosal nerve involves the step of applying a stimulus to the nerve to evoke a sub-maximal tumescence of the penis such that subsequent tumescence responses to subsequently applied stimuli occur more rapidly.

For priming of the cavernosal nerve, the ground or reference should be located near the midline caudal to the stimulation site (not laterally or to the side of the site). After grounding the patient, the operator places the probe of the device as previously described adjacent to the approximate location of the cavernosal nerve so that the array spans its possible locus. Sustained (as opposed to pulsatile) stimuli having an intensity capable of evoking a sub-saturation criterion response are applied to the nerve via the array of the apparatus. Stimuli of such an intensity are applied to the nerve in accordance with the pre-defined electrode sequence to evoke an initial tumescent response, which will expedite the onset of subsequent tumescence responses to subsequently applied stimuli. Following the priming step, the response to effective stimulation of the cavernosal nerve will occur more rapidly and on a larger magnitude.

The parameters for priming of the cavernosal nerve are preferably set at 2–8 mA, 800 μs, and 16 Hz. Such parameters have been found to evoke a sub-saturation criterion response desirable for priming of the nerve. Naturally, the parameters of the priming stimuli may be varied so long as the priming stimuli are capable of evoking a sub-saturation response.

To prime the cavernosal nerve using a single electrode, the electrode is passed over the area believed to be the location of the target nerve, while simultaneously applying stimulus pulses of the above-described parameters. The user continues to sweep the electrode over the target area until the nerve has been sufficiently primed.

Location of the Cavernosal Nerve

After priming the cavernosal nerve (or in the case where priming is deemed unnecessary), the same may be located using the array probe of the present invention in accordance with the following method. The method for locating the cavernosal nerve generally comprises the steps of a) applying a stimulus to the nerve to evoke a tumescence response, b) detecting a tumescence response to stimulation of the nerve, c) evaluating the tumescence response to stimulation of the nerve, and d) automatically modifying the site of subsequent stimulation based on the evaluation of the tumescence response. The method is unique in that the stimulus is of a low intensity known to stimulate the nerve when the site of stimulation within 1–2 mm of the nerve. The method is also unique due to the fact that the steps of evaluating the response and modifying the site of stimulation are performed automatically by a control means.

To locate the nerve using the apparatus of the invention, the device is switched to the locating mode of operation. Upon initiating the locating mode, the electrode selecting algorithm of the control means initiates a pre-arranged sequence among all or part of the electrode array. A pulsed stimulus train is applied to the nerve in accordance with a pre-arranged electrode sequence. The parameters of the stimulus train are set at an intensity known to stimulate the nerve when the stimulating electrode is within 1.0 mm of the nerve. For localization of the cavernosal nerve, such parameters are set at 2–4 mA, 500 μs, 16 Hz. The stimuli to be applied to the nerve may be pulsed (as opposed to sustained) as changes in the response pattern to pulsed stimuli (i.e., increases or decreases in penile tumescence) are easier to distinguish and interpret than changes in the response pattern to sustained stimuli.

Changes in the response pattern are detected and measured by the response measuring means of the apparatus. For location of the cavernosal nerve, the response measuring means is preferably a tumescence monitor comprising mercury-filled distensible tubing. Naturally, any one of the other means described in this application for detecting and measuring tumescence of the penis is equally suitable for achieving the objectives of the present invention.

Response feedback information (that is, information concerning an increase or decrease in tumescence) is sent to the control means, where the control means interprets the change in the tumescent response in light of the stimulation and response history of the cavernosal nerve. Based on the change in the response pattern, the control means determines which electrodes were most effective in stimulating the cavernosal nerve and formulates and applies a second sequence of stimulating pulses to the nerve by those electrodes found to be most effective. The program continues to run until the control means identifies which electrode is most effective at stimulating the nerve at an intensity known to stimulate the nerve at a distance of 1 mm or less. At this stage in the method, the stimulus pulse may be decreased to approximately 1–3 mA to confirm that the cavernosal nerve is indeed below the identified electrode.

By localizing the cavernosal nerve, the same can be spared during the excision of tumorous tissue of the prostate. Following excision of tissue, the apparatus may be used again in the manner previously described to confirm that the cavernosal nerve has been spared and remains functional.

Although specific parameters are listed above for both priming and locating of the cavernosal nerve, the stimulus parameters may vary within the following ranges:

0.5–25 mA: Stimulation above 8 mA intensity diminishes spatial resolution while less current will make it easier to miss the effect altogether because the electrode will have to be right on the nerve for effective stimulation to take place. At 4–8 mA the electrode will activate the nerve from 1–2 mm away.

200–2000 μs: Durations of less than 200 μs result in individual pulse intensities which are too high. Longer durations add little nerve stimulating effect to each pulse.

4–50 Hz: Lower frequencies require a longer time period to activate the nerve response, while higher frequencies are associated with diminished responses over the long term.

Alternative Embodiments and Applications
Alternative Electrode Configurations

Figure 7:
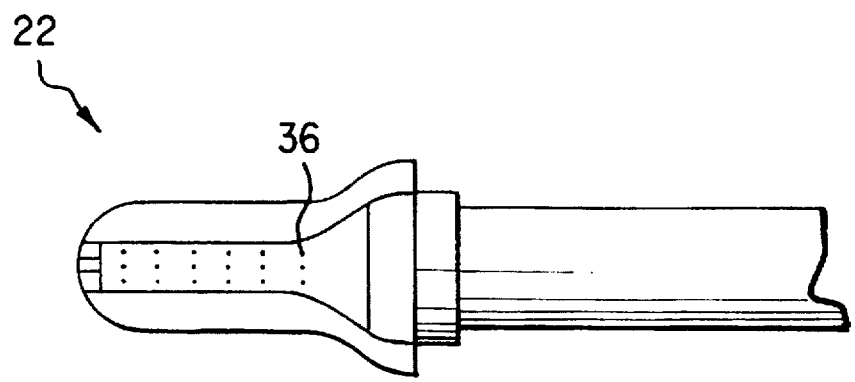
FIG. 7 illustrates another embodiment of the array probe of the present of the invention.

Although the electrodes of the array have been described as being spaced in a one dimensional or linear relationship, this is not to say that the electrodes of the array may not be otherwise arranged. Indeed, the electrodes of the array may be arranged in a non-linear (i.e., curved) arrangement or two (or multi) dimensionally as illustrated in FIG. 7. Where the electrodes are arranged two dimensionally, they may be arranged in a grid-like formation. In one aspect, this grid may be used to map the longitudinal axis and symmetry of the target nerve. To map the axis of the nerve, a stimulation method of successive triplets is applied. Using the successive triplet method, 20–50 electrodes are arranged in a grid-like formation such that a cathode is surrounded on either side by an anode. The triplets of electrodes are then activated in accordance with a triplet selecting algorithm to identify the longitudinal axis of the nerve. For reasons known to those skilled in the art of stimulating nerve axons, those triplets positioned orthogonal to the axis of the nerve will be less effective at stimulating the nerve than those triplets positioned in line with the axis.

The two-dimensional, grid-like configuration is especially beneficial for optimal stimulation purposes (discussed below), as the electrode selecting algorithm of the apparatus is capable of locating the nerve (by switching among the electrodes of the grid) to thereafter maximally stimulate the nerve by combined stimulation of the individual electrodes each capable of independently increasing or causing a response.

Nerve Localization and Stimulation for Therapeutic Purposes

It is envisioned that the apparatus of the present invention may be used for therapeutic purposes such as for the treatment of impotence. When stimulating a nerve for a therapeutic purpose (either intraoperatively, transcutaneously, transrectally or through an implant) the goal is to optimally stimulate the nerve with a stimulus of the lowest possible intensity to avoid potential undesired effects such as patient pain, muscular twitches, urination, defecation, or toxicity from ion deposition from the electrodes. The apparatus of the present invention is especially suited for this purpose in light of the fact that the apparatus is capable of automatically locating and stimulating a nerve using a single device comprising small, closely-spaced electrodes activated at low stimulus intensities. The apparatus eliminates reliance on the skill of the operator to enable precise location of nerves difficult to see without a microscope (such as the cavernosal nerve). The apparatus of the device is also superior over prior stimulating devices because it does not utilize cuff electrodes which tend to degenerate or deteriorate the nerve.

To optimally stimulate the cavernosal nerve using the device of FIG. 1, probe 12 is first inserted within the rectum to locate the same. The nerve is located by the apparatus in accordance with the priming and/or locating methods previously described in this application. After locating the nerve, the electrodes closest to the nerve are repeatedly fired to optimally stimulate the nerve. If the operator wishes to stimulate the branches of the cavernosal nerve, multiple electrodes of the array may be activated in a rapid sequential manner to optimally stimulate all branches of the nerve.

Because the array of the apparatus utilizes small, closely spaced electrodes, the apparatus is capable of stimulating the cavernosal nerve and any of its branches without causing the undesired effects described above, particularly that of pain. In fact, stimulation of the cavernosal nerve via the small-diameter electrodes of the present invention is more effective (and efficient) than stimulation of the nerve by a larger electrode, as the current density of a low-intensity stimulus applied directly to the nerve by a small electrode is greater than the current density of the high-intensity stimulus required to activate the nerve by a large electrode even at the same distance.

Figure 2:
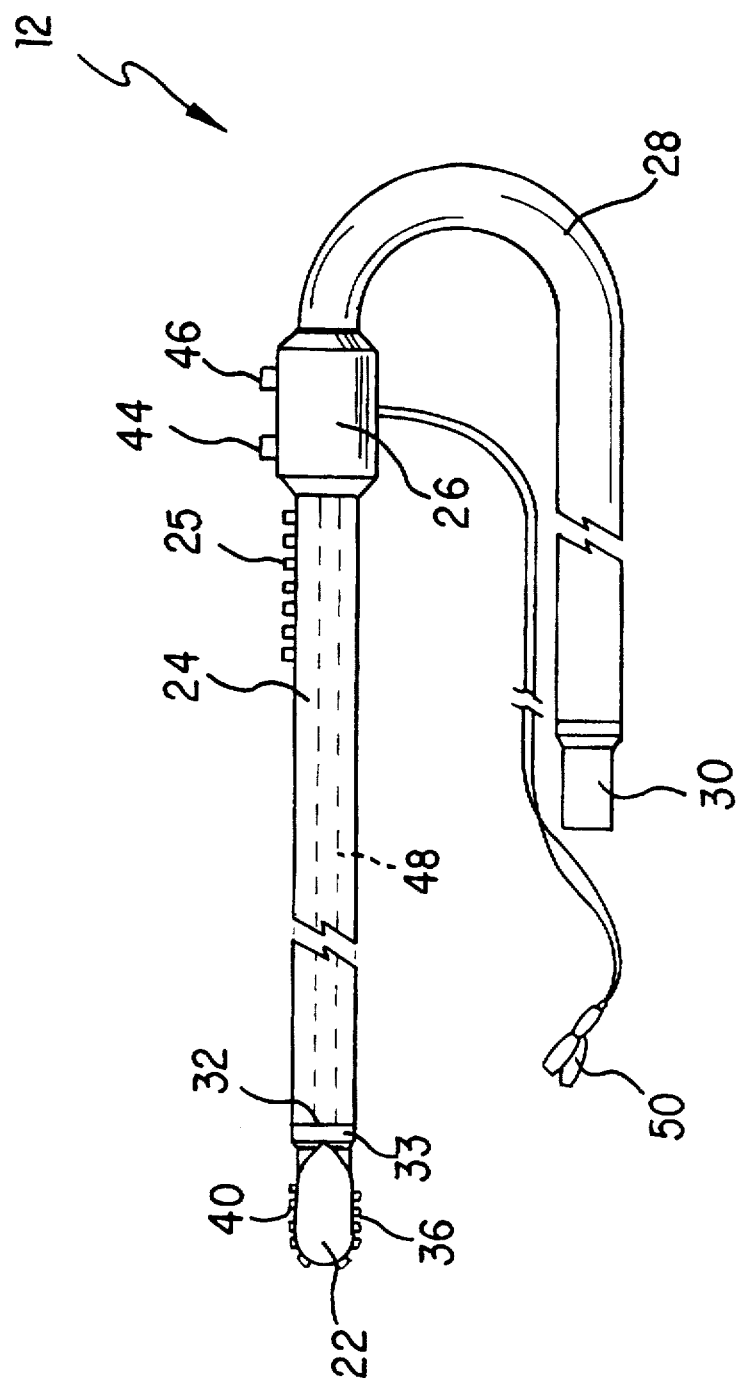
FIG. 2 is a side elevational view of the array probe component.

Although the probe shown in FIGS. 1–3 may be used to locate and optimally stimulate the cavernosal nerve (or any other nerve), a probe having an electrode array configured multi dimensionally may be used.

Alternatively, the stimulus applying means of the apparatus may be configured as an implant which may be surgically implanted within the body, adhesively applied to the skin, or inserted into a natural body cavity including, but not limited to, the rectum, vagina or urethra.

The implant in combination with the automated control and response detection means of the present invention enables precise localization and optimal stimulation of a nerve and any of its associated branches. Naturally, the implant should be capable of conforming to the tissue of the body or the body cavity into which it is inserted.

Figure 8:
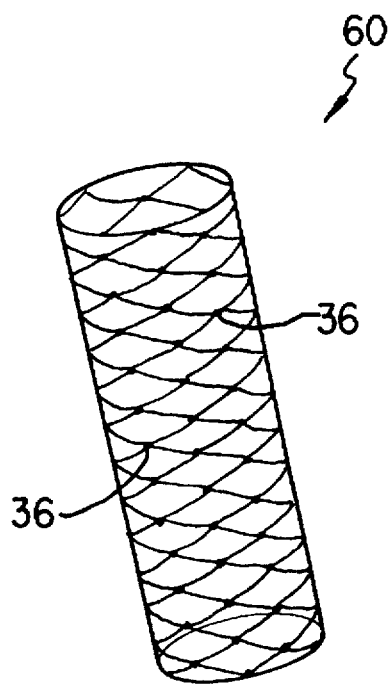
FIG. 8 illustrates an expandable stent having a plurality of electrodes.

An implant which may be inserted into a natural body cavity is shown in FIG. 8. This implant takes the form of an expandable stent 60 provided with a plurality of electrodes 36. Stent 60 may be coupled to the apparatus of FIG. 1 in place of probe 12 for the purpose of locating and optimally stimulating a nerve as previously described.

Figure 8A:
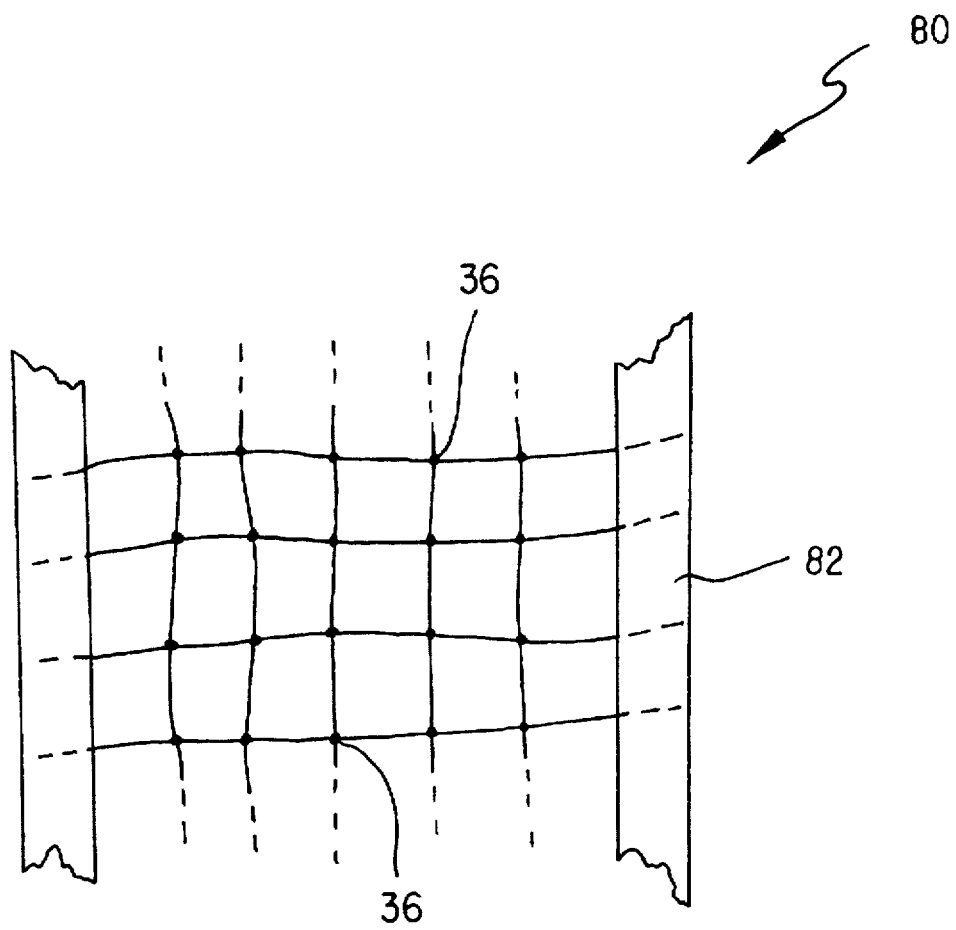
FIG. 8A illustrates a patch having a plurality of electrodes.

For the transcutaneous stimulation of a nerve, it is envisioned that the electrode array may be configured as a patch 80, as shown in FIG. 8A, which may be affixed to the skin by a suitable adhesive 82. Akin to the probe of the apparatus, patch 80 may be provided with an array of stimulating electrodes 36 positioned in a grid-like or other formation. Transcutaneous stimulation of a nerve is accomplished by first locating the nerve (via the patch) using the method previously described. After locating the nerve, the electrode (or electrodes) found to be most effective at stimulating the nerve are activated to optimally stimulate the nerve.

Naturally, the implant may take a form other than that suggested herein, the form of the implant being dependent upon the nerve to be located and its location within the tissues of the body.

An advantage of the implant embodiment of the present invention over prior implants is that the device takes into account shifts in tissue which may result in misalignment of the target nerve with the electrodes of the array. In order to reestablish localization of the nerve, the operator need only re-run the priming and locating steps of the apparatus to re-locate the nerve for optimal stimulation purposes. There is no need to remove the implant or reposition the same, in light of the fact that the array of electrodes is capable of stimulating the tissue of the body cavity at various sites.

It is also envisioned that the array probe may be used to identify and locate the severed end of a nerve so that reattachment of the nerve can be performed.

Alternative Means for Automatically Varying the Stimulation Site

As stated previously in this application, one of the advantages of the present invention over the prior art is the provision of a means for automatically varying the site of stimulation in response to information provided by the response detection means. Although the electrode array is well-suited to achieve the objectives of the present invention, other means for automatically varying the location of the stimulation site have been envisioned. One such device is a magnetic sphere which utilizes three magnetic induction coils which are positioned orthogonally with respect to each other to magnetically induce a current in a specific site. The induced current may be focused as dictated by the control means of the invention to apply a stimulus to a particular area for the purpose of activating and localizing a target nerve. A suitable magnetic sphere is disclosed in U.S. Pat. No. 4,905,698 to Clir-Strohl et al., the disclosure of which is incorporated herein by reference. The magnetic sphere of the Clir-Strohl et al. patent is commercially available from Navion, Stoughton, Mass.

Figure 11:
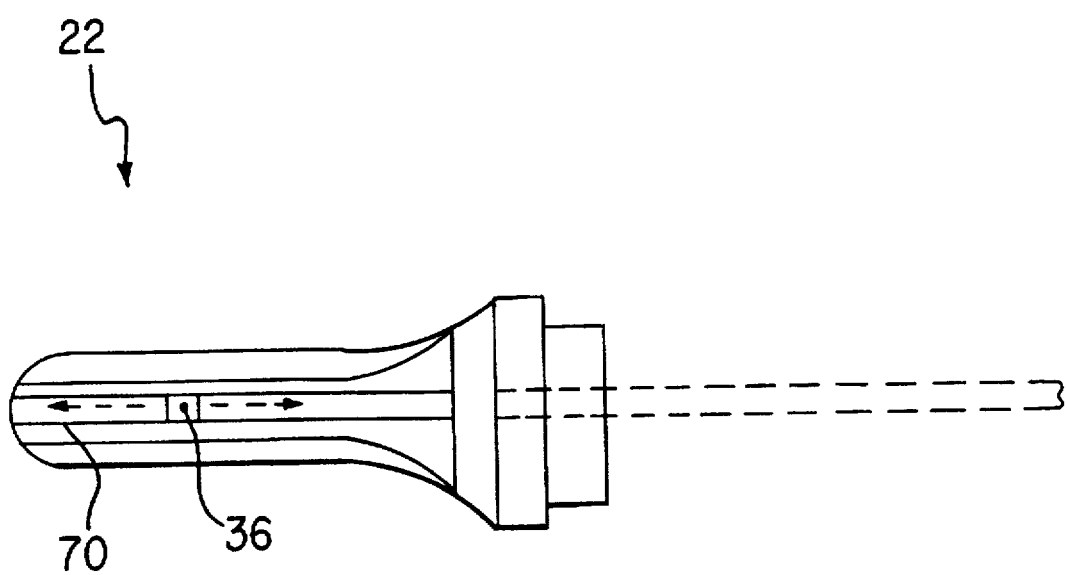
FIG. 11 is an illustration of an alternative stimulating device for automatically varying the site of stimulation.

Yet another device for varying the site of stimulation is a single, small electrode movably positioned on a track. With reference to FIG. 11, the site of stimulation is altered by moving electrode 36 along a track 70 in accordance with an electrode positioning algorithm governed by the control means of the invention. By moving the electrode along the track, the exact location of the target nerve may be determined by the method previously described.

It should be understood that although not specifically described herein, other means capable of altering the site of stimulation are appropriate for accomplishing the objectives of the present invention.

The foregoing description is considered to be illustrative of the principles of the present invention. It is not intended to limit the scope of the invention, as the same may be practiced otherwise than as specifically described herein. The scope of the invention is hereby defined by the following claims.

We claim:

1. An apparatus for stimulating and locating a nerve, comprising:
    means for applying a stimulus to a plurality of sites within an area of tissue likely to contain the nerve to be located;
    means for detecting a response to said stimulus;
    means for automatically modifying the site of stimulation, said means for automatically modifying the site of stimulation including means for interpreting the response provided by said response detecting means; and
    means for indicating the location of the nerve to the user;
    wherein said modifying means automatically modifies the site of a stimulus applied to the area of tissue likely to contain the nerve based on an interpretation of the detected response by said interpreting means to further stimulate the nerve to determine its location.

2. The apparatus of claim 1, wherein said means for applying a stimulus to a plurality of sites within an area of tissue likely to contain the nerve to be located applies said stimulus transcutaneously.

3. The apparatus of claim 1, wherein said means for applying a stimulus comprises a probe for applying the stimulus to an operative site within the area of tissue likely to contain the nerve to be located.

4. The apparatus of claim 1, wherein said means for applying a stimulus to a plurality of sites within an area of tissue likely to contain the nerve to be located applies said stimulus to the plurality of sites via a natural body orifice.

5. The apparatus of claim 1, wherein said means for applying a stimulus to a plurality of sites within an area of tissue likely to contain the nerve to be located is a magnetic induction device capable of focusing a magnetic field to induce an electrical stimulating current.

6. The apparatus of claim 1, wherein said means for applying a stimulus to a plurality of sites within an area of tissue likely to contain the nerve to be located is an array of electrodes.

7. The apparatus of claim 1, wherein said means for applying a stimulus to a plurality of sites within an area of tissue likely to contain the nerve to be located is a patch comprising an array of electrodes.

8. The apparatus of claim 1, wherein said means for applying a stimulus to a plurality of sites within an area of tissue likely to contain the nerve to be located comprises an electrode movably positioned on a track.

9. The apparatus of claim 6, wherein said electrodes are arranged in a multi-dimensional configuration.

10. The apparatus of claim 6, wherein said array includes 20–50 electrodes.

11. The apparatus of claim 6, wherein said electrodes are spaced 0.1–4.0 mm apart.

12. The apparatus of claim 1 further comprising a stimulator circuit disposed in connection with said stimulus applying means for generating a stimulus comprising a train of multiple pulses.

13. The apparatus of claim 9, wherein said electrodes are activated in successive triplets to determine the longitudinal axis and symmetry of the nerve.

14. The apparatus of claim 1, wherein said modifying means further comprises:
    memory for storing parameters of response states which correspond to successful and unsuccessful stimulation of the nerve, and recording means for recording and storing the response provided by said response detection means, wherein said interpreting means interprets data received from said response detection means and stored in said recording means, and wherein said interpreting means discriminates between states corresponding to periods of successful stimulation and states corresponding to periods of unsuccessful stimulation by comparing the response provided by said response detection means with the parameters stored in said memory.

15. The apparatus of claim 1, wherein said modifying means is a microprocessor comprising:
    memory for storing parameters of response states which correspond to successful and unsuccessful stimulation of the nerve; and
    recording means for recording and storing the response provided by said response detection means,
    wherein said microprocessor is coupled to said stimulus applying means by a first coupling means and said microprocessor is coupled to said response detecting means by a second coupling means.

16. The apparatus of claim 1, wherein said modifying means further comprises memory for storing an electrode selecting algorithm and said modifying means modifies subsequent application of the stimulus applied by said stimulus applying means in accordance with said electrode selecting algorithm.

17. The apparatus of claim 1, wherein said stimulus applying means is a probe used intraoperatively.

18. The apparatus of claim 1, wherein said means for detecting a response to a stimulus is an ultrasonic density gauge.

19. An apparatus for stimulating and locating the cavernosal nerve, comprising:
- a stimulator circuit for generating a stimulus;
- a probe disposed in connection with said stimulator circuit, said probe having a handle portion and a stimulating tip for applying a stimulus to an area of tissue likely to contain the nerve to be located, said stimulating tip comprising an array of electrodes;
- a control means for governing activation of said array of electrodes, said control means comprising:
    - memory for storing an electrode selecting algorithm which activates the electrodes of said array based on an evaluation of a change in a tumescence response to successful stimulation of the cavernosal nerve; and
    - means for employing the electrode selecting algorithm; and
- a response detection means for detecting and measuring a tumescence response, wherein said response detection means provides tumescence response information to said control means for evaluation by said electrode selecting algorithm to further stimulate the nerve to determine its location.

20. The apparatus of claim 19, wherein said stimulator circuit generates a stimulus comprising a train of pulses.

21. The apparatus of claim 19, wherein said electrodes are spaced 1.0 mm apart.

22. The apparatus of claim 19, wherein said array of electrodes comprises 4–16 electrodes.

23. The apparatus of claim 19, wherein said response detection means is a tumescence monitor comprising distensible tubing filled with a conductive fluid in electrical contact with said control means.

24. The apparatus of claim 19, wherein said stimulator circuit generates a stimulus having parameters which range between 0.5–25 mA, 100–2000 μs, 4–50 Hz.

25. The apparatus of claim 19 further comprising a suction port for the removal of bodily fluids from the surgical field.

26. The apparatus of claim 19, further comprising a filter to isolate the change in the tumescence response from changes induced by surgical intervention while locating the nerve with the apparatus.

27. The apparatus of claim 19, wherein said probe includes a longitudinal axis and the most distal electrode of said array is angled at approximately 45° with respect to the longitudinal axis of said probe to position the most distal electrode below the prostate gland or urethra of a patient.

28. The apparatus of claim 19, wherein said handle of said probe is flexible to enable positioning of the probe within the body tissue.

29. The apparatus of claim 19, wherein said apparatus further includes a means for indicating the location of the nerve to the user.

30. An apparatus for locating and optimally stimulating a nerve, comprising:
- an implant comprising an array of electrodes for delivering a stimulus to a nerve;
- a control means for governing activation of said electrodes of said array, said array of electrodes being activated in accordance with an electrode selecting algorithm which evaluates a response to successful stimulation of the nerve; and
- a response detection means for detecting and measuring a response, said response detection means providing response feedback information to said control means for evaluation by said electrode selecting algorithm.

31. The apparatus of claim 30, wherein said electrodes are positioned in a multi-dimensional formation.

32. The apparatus of claim 30, wherein said electrodes are spaced 0.1–4.0 mm apart.

33. The apparatus of claim 30, wherein a selected subset of said electrodes are determined to be near the nerve and are activated in rapid sequence to optimally stimulate the nerve.

34. The apparatus of claim 30, wherein said nerve is the cavernosal nerve.

35. The apparatus of claim 30, wherein said implant is a stent inserted within a natural body cavity of the patient.

36. The apparatus of claim 34, wherein said response detection means is a tumescence monitor.

37. A method for stimulating the cavernosal nerve comprising the step of:
- applying a stimulus, said stimulus being capable of initiating sub-maximal tumescence of the penis such that subsequent tumescence responses to subsequently applied stimuli occur with shorter delay from the onset of successful stimulation.

38. The method of claim 37, wherein said stimulus is a train of electrical pulses.

39. The method of claim 38, wherein the parameters of said stimulus are within the range of 0.5–25 mA, 100–2000 μs, 4–50 Hz.

40. The method of claim 38, wherein said stimulus is applied to the nerve by a probe having an array of electrodes.

41. The method of claim 40, wherein said array comprises 4–16 electrodes.

42. The method of claim 37, wherein said stimulus is a drug capable of evoking a tumescence response.

43. The method of claim 42, wherein said drug is papaverine.

44. The method of claim 37, wherein said stimulus is a vibrating pulse.

45. A method for stimulating and locating the cavernosal nerve, comprising the steps of:
- (a) applying a stimulus to a tissue site likely to contain the nerve to be located to evoke a tumescence response, the stimulus having an intensity known to stimulate the nerve when the site of stimulation is within a known distance from the nerve;
- (b) detecting a tumescence response to stimulation of the nerve;
- (c) evaluating the tumescence response to stimulation of the nerve; and
- (d) automatically modifying the site of subsequent stimulation based on the evaluation of the tumescence response to further stimulate the nerve to determine its location.

46. The method of claim 45, wherein said applying step comprises the step of generating a stimulus of an intensity known to stimulate the cavernosal nerve when the site of stimulation is within 1 mm of the nerve.

47. The method of claim 45 further comprising the step of repeating steps (a)–(d) until localization of the nerve is achieved.

48. The method of claim 47 further comprising the step of indicating to the user the location of the nerve.

49. The method of claim 45, wherein said applying step is performed by a probe having an array of electrodes.

50. The method of claim 45, wherein said applying step is performed by an implant having an array of electrodes positioned in a multi-dimensional arrangement.

51. The method of claim 50, wherein said applying step further comprises the step of activating the electrodes of said implant in successive triplets to determine the longitudinal axis of the nerve to optimally stimulate the nerve.

52. The method of claim 45, wherein said applying step comprises the step of generating a stimulus comprising a current pulse of 0.5–25 mA.

53. The method of claim 45, wherein said applying step comprises the step of generating a stimulus comprising a train of pulses.

54. The method of claim 45, wherein said detecting step is performed by a tumescence monitor which detects successful stimulation of the cavernosal nerve.

55. The method of claim 54, wherein said evaluating step is performed by a response interpreting means which interprets a change in the tumescence response.

56. The method of claim 49, wherein said modifying step is performed by a modifying means comprising a memory which automatically modifies the site of stimulation among the electrodes of said array in accordance with an electrode selecting algorithm stored in said memory.

57. The method of claim 45 further comprising the step of priming the nerve by applying a stimulus to the nerve, said stimulus being capable of initiating sub-maximal tumescence of the penis such that subsequent tumescence responses to subsequently applied stimuli occur with shorter delay from the onset of successful stimulation, and wherein said priming step is performed prior to step (a).

58. A method for locating a nerve, comprising the steps of:
(a) applying a stimulus to a tissue site likely to contain the nerve to be located;
(b) detecting a response to stimulation of the nerve;
(c) evaluating the response to successful stimulation of the nerve; and
(d) automatically modifying the site of subsequent stimulation based on the evaluation of the response to further stimulate the nerve to determine its location.

59. The method of claim 58, wherein said applying step comprises the step of generating a stimulus of an intensity known to stimulate the nerve when the site of stimulation is within a known distance from the nerve.

60. The method of claim 58 further comprising the step of repeating said steps (a)–(d) until localization of the nerve is achieved.

61. The method of claim 60, further comprising the step of indicating to the user the location of the nerve.

62. The method of claim 58, wherein said applying step is performed by an instrument including an array of electrodes.

63. The method of claim 58, wherein said modifying step is performed by a modifying means which automatically modifies the site of stimulation in accordance with a site selecting algorithm which is based on information provided by a response detecting means and stimulation input means.

64. An apparatus for locating a nerve, comprising:
a source of electricity;
a stimulus applying means coupled to said source of electricity for applying a stimulus to an area of tissue likely to contain the nerve to be located, said stimulus applying means including an array of electrodes;
means for detecting a response to said stimulus;
means for varying activation of the electrodes of said array; and
indicating means for indicating location of the nerve to the user,
wherein said activation means varies activation of the electrodes of said array based on the detected response to the stimulus applied by said stimulus applying means to further stimulate the nerve to determine its location.

65. A method for stimulating and locating the cavernosal nerve, comprising the steps of:
(a) applying a low intensity stimulus to a tissue site likely to contain the nerve to evoke a sub-maximal tumescence response, said stimulus having an intensity known to stimulate the nerve when the site of stimulation is within a minimal distance from the nerve;
(b) detecting a tumescence response to stimulation of the nerve;
(c) evaluating the differential of the tumescence response to stimulation of the nerve;
(d) automatically modifying the site of subsequent stimulation based on the evaluation of the differential of the tumescence response to further stimulate the nerve to determine its location.

66. The method of claim 65 further comprising the step of repeating steps (a)–(d) until localization of the nerve is achieved.

67. The method of claim 66, further comprising the step of indicating to the user the location of the nerve.

68. The method of claim 65, wherein said applying step is performed by an array of electrodes, each electrode of said array having a diameter less than 2 mm.

69. An apparatus for stimulating and locating a nerve, comprising:
means for applying a stimulus to a plurality of sites within an area of tissue likely to contain the nerve to be located;
means for detecting and measuring a response to said stimulus;
means for automatically modifying the site of stimulation within the area of tissue likely to contain the nerve to be located;
means for determining the location of the nerve to be located, wherein said means for determining the location of the nerve evaluates the responses elicited by application of a stimulus to each of said plurality of sites to determine the location of the nerve; and
means for indicating the location of the nerve to the operator.

70. The apparatus of claim 69, wherein said applying means is a probe.

71. The apparatus of claim 70, wherein said probe comprises an array of electrodes.

72. The apparatus of claim 71 further comprising memory and wherein said modifying means automatically modifies the site of stimulation by activating said array of electrodes in accordance with a predefined electrode activating program stored in said memory.

73. The apparatus of claim 72, wherein said array comprises 8 electrodes.

74. The apparatus of claim 69, wherein the nerve to be located is the cavernosal nerve and said means for detecting and measuring a response is a tumescence monitor.

75. The apparatus of claim 69, wherein said modifying means automatically modifies the site of stimulation in accordance with a predefined program.

76. The apparatus of claim 75 further comprising memory for storing said predefined program for automatically modifying the site of stimulation.

77. The apparatus of claim 76, wherein said memory contains at least one predefined program.

78. The apparatus of claim 69 further comprising recording means for recording and storing the responses provided by said response detecting and measuring means and wherein the differential of the responses stored in said recording means is evaluated and compared by said location determining means.

79. A method for locating a nerve, comprising the steps of:
   (a) applying a stimulus to a site within an area of tissue likely to contain the nerve to be located;
   (b) detecting a response to stimulation of the nerve;
   (c) measuring the detected response; and
   (d) automatically modifying the site of subsequent stimulation in accordance with a predefined site selecting program.

80. The method of claim 79 further comprising the steps of:
   (e) applying a subsequent stimulus to the tissue site as modified in accordance with said predefined site selecting program;
   (f) detecting a response to the subsequent stimulus; and
   (g) comparing the differential of the detected responses to determine the location of the nerve.

81. The method of claim 80 further comprising the step of:
   (h) repeating steps (a)-(g).

82. The method of claim 81 further comprising the step of:
   (i) indicating the location of the nerve to the operator.

83. The method of claim 80 further comprising the step of:
   (h) indicating the location of the nerve to the operator.

84. The method of claim 79, wherein said applying step is performed by an array of electrodes positioned on a probe.

85. The method of claim 84, wherein the nerve to be located is the cavernosal nerve and wherein said detecting step is performed by a tumescence monitor.

86. The method of claim 79, wherein said modifying step is performed by a modifying means comprising memory for storing said predefined site selecting program.

87. An apparatus for stimulating and locating a nerve, comprising:
   means for applying a stimulus to a plurality of sites within an area of tissue likely to contain the nerve to be located;
   means for detecting and measuring a response to said stimulus;
   means for determining the location of the nerve to be located, wherein said means for determining the location of the nerve evaluates the responses elicited by application of a stimulus to each of said plurality of sites within the area of tissue likely to contain the nerve to determine the location of the nerve; and
   means for indicating the location of the nerve to the user.

88. The apparatus of claim 87, wherein said applying means is a probe comprising at least one electrode.

89. The apparatus of claim 87, wherein the nerve to be located is the cavernosal nerve and said means for detecting and measuring a response is a tumescence monitor.

90. The apparatus of claim 87 further comprising recording means for recording and storing the responses provided by said response detecting and measuring means and wherein the differential of the responses stored in said recording means is evaluated and compared by said location determining means.

91. A method for locating a nerve, comprising the steps of:
   (a) applying a stimulus to a site within an area of tissue likely to contain the nerve to be located;
   (b) detecting a response to stimulation of the nerve;
   (c) measuring the detected response;
   (d) modifying the site of subsequent stimulation;
   (e) applying a subsequent stimulus to the modified site of stimulation; and
   (f) evaluating the detected responses elicited by application of a stimulus to each of the stimulation sites to determine the location of the nerve.

92. The method of claim 91 further comprising the step of:
   (g) repeating steps (a)-(f).

93. The method of claim 92 further comprising the step of:
   (h) indicating the location of the nerve.

94. The method of claim 91 further comprising the step of:
   (g) indicating the location of the nerve.

95. The method of claim 91, wherein said applying step is performed by an array of electrodes positioned on a probe.

96. The method of claim 95, wherein said modifying step is performed automatically by a modifying means comprising memory for storing a predefined site selecting program and wherein the electrodes of said array are activated in accordance with said site selecting program.

97. The method of claim 91, wherein the nerve to be located is the cavernosal nerve and wherein said detecting step is performed by a tumescence monitor.

98. The method of claim 91, wherein said applying step is performed by a single electrode positioned on a probe.

99. The method of claim 98, wherein said modifying step is performed manually.

* * * * *